United States Patent
Aithani et al.

(10) Patent No.: US 12,211,588 B1
(45) Date of Patent: Jan. 28, 2025

(54) METHODS AND SYSTEMS FOR USING DEEP LEARNING TO PREDICT PROTEIN-LIGAND COMPLEX STRUCTURES IN PROTEIN FOLDING AND PROTEIN-LIGAND CO-FOLDING

(71) Applicant: Charm Therapeutics Limited, London (GB)

(72) Inventors: Lakshyaditya Singh Aithani, Oxford (GB); Liam Atkinson, Padua (IT)

(73) Assignee: Charm Therapeutics Limited, London (GB)

( * ) Notice: Subject to any disclaimer, the term of this patent is extended or adjusted under 35 U.S.C. 154(b) by 0 days.

(21) Appl. No.: 18/479,524

(22) Filed: Oct. 2, 2023

Related U.S. Application Data

(60) Provisional application No. 63/411,676, filed on Sep. 30, 2022.

(51) Int. Cl.
 G01N 33/48 (2006.01)
 G16B 15/20 (2019.01)
 G16B 15/30 (2019.01)

(52) U.S. Cl.
 CPC ............ *G16B 15/30* (2019.02); *G16B 15/20* (2019.02)

(58) Field of Classification Search
 None
 See application file for complete search history.

(56) References Cited

U.S. PATENT DOCUMENTS

2021/0166779 A1  6/2021  Jumper et al.

FOREIGN PATENT DOCUMENTS

| WO | WO-2020058174 A1 | 3/2020 |
| WO | WO-2020058176 A1 | 3/2020 |
| WO | WO-2020058177 A1 | 3/2020 |
| WO | WO-2020210591 A1 | 10/2020 |
| WO | WO-2021110730 A1 | 6/2021 |

OTHER PUBLICATIONS

Yan, Xu, et al. "PointSite: a point cloud segmentation tool for identification of protein ligand binding atoms." Journal of Chemical Information and Modeling 62.11 (2022): 2835-2845.*
Ahdritz, et al., aqlaboratory/openfold: OpenFold v1.0.1, Nov. 12, 2021.
Alcaide, et al., MP-NeRF: A massively parallel method for accelerating protein structure reconstruction from internal coordinates, Journal of Computational Chemistry, Jan. 2022, pp. 74-78.
Berman, et al., The protein data bank, Nucleic Acids Research, 2000, pp. 235-242.
Eberhardt, et al., AutoDock Vina 1.2. 0: New docking methods, expanded force field, and python bindings, Journal of Chemical Information and Modeling, Jul. 2021, pp. 3891-3898.
Du, et al., Insights into protein-ligand interactions: mechanisms, models, and methods, International Journal of Molecular Sciences, Jan. 2016, 34 pages.
Frimurer, et al., Ligand-induced conformational changes: improved predictions of ligand binding conformations and affinities, Biophysical Journal, Apr. 2003, pp. 2273-2281.
Ganea, et al., Geomol: Torsional geometric generation of molecular 3d conformer ensembles, Advances in Neural Information Processing Systems, Dec. 2021, pp. 13757-13769.
Grover, Use of allosteric targets in the discovery of safer drugs, Medical Principles and Practice, Sep. 2013, pp. 418-426.
Hassan, et al., Protein-ligand blind docking using QuickVina-W with inter-process spatio-temporal integration, Scientific Reports, Nov. 2017, 13 pages.
Jumper, et al., Highly accurate protein structure prediction with AlphaFold, Nature, Aug. 2021, pp. 583-589.
Kabsch, et al., A solution for the best rotation to relate two sets of vectors, Acta Crystallographica Section A: Crystal Physics, Diffraction, Theoretical and General Crystallography, Sep. 1976, pp. 922-923.
Koes, et al., Lessons learned in empirical scoring with smina from the CSAR 2011 benchmarking exercise, Journal of Chemical Information and Modeling, Aug. 2013, pp. 1893-1904.
McNutt, et al., GNINA 1.0: molecular docking with deep learning, Journal of Cheminformatics, Dec. 2021, 43 pages.
Stark, et al., EquiBind: Geometric deep learning for drug binding structure prediction, International Conference on Machine Learning, Jun. 2022, pp. pp. 20503-20521.
Sverrisson, et al., Fast end-to-end learning on protein surfaces, Proceedings of the IEEE/CVF Conference on Computer Vision and Pattern Recognition, 2021, pp. 15272-15281.
Trott, et al., AutoDock Vina: improving the speed and accuracy of docking with a new scoring function, efficient optimization, and multithreading, Journal of Computational Chemistry, Jan. 2010, pp. 455-461.
Wang, et al., The PDBbind database: Collection of binding affinities for protein-ligand complexes with known three-dimensional structures, Journal of Medicinal Chemistry, Jun. 2004, pp. 2977-2980.

\* cited by examiner

*Primary Examiner* — Anna Skibinsky
(74) *Attorney, Agent, or Firm* — COOLEY LLP

(57) ABSTRACT

A method for using machine learning to predict protein-ligand complex structures in protein folding and/or protein-ligand co-folding is presented. The method includes receiving, at a processor, a predicted set of coordinates for (1) a plurality of protein atoms and (2) a plurality of ligand atoms, included in a protein-ligand structure. At least one adjustment to be applied to the predicted set of coordinates is determined based on a plurality of loss functions associated with the plurality of protein atoms and/or the plurality of ligand atoms. A machine learning model is trained to predict geometric information of an unseen protein-ligand structure based on the at least one adjustment.

20 Claims, 8 Drawing Sheets

500

METHODS AND SYSTEMS FOR USING DEEP LEARNING TO PREDICT PROTEIN-LIGAND COMPLEX STRUCTURES IN PROTEIN FOLDING AND PROTEIN-LIGAND CO-FOLDING

CROSS-REFERENCE TO RELATED APPLICATIONS

This application claims the benefit and priority to U.S. Patent Application No. 63/411,676, filed Sep. 30, 2022, the contents of which are hereby incorporated by reference.

BACKGROUND

Structure based drugs are designed to predict the conformation, orientation and location of a ligand when bound to a protein of interest, as this is related to the mechanism of action and biological effect. Known target-based discovery in the pharmaceutical industry can be expensive and time consuming because of low chemical space coverage in screening decks. Known docking software used for screens in target-based approaches underperforms in situations where true holoprotein structure is unknown. Moreover, known target-based approaches use a known three-dimensional (3D) structure of a protein and binding site while also not predicting induced fit of the protein. Additionally, some known docking software programs that simulate the protein-ligand (P-L) binding event and return have the flaws of generating a set of selected poses, which theoretically have a high likelihood of being the native pose of a protein. Thus, a need exists for a neural network that predicts not only the crystal pose of a ligand, but also the induced fit of the protein.

SUMMARY

In an embodiment, a non-transitory processor-readable medium stores code representing instructions to be executed by one or more processors, the instructions including code to cause the one or more processors to receive a predicted set of coordinates for (1) a plurality of protein atoms and (2) a plurality of ligand atoms, included in a protein-ligand structure. The code also causes the one or more processors to determine at least one adjustment to be applied to the predicted set of coordinates based on (a) at least one first loss function configured to determine at least one translation difference between the predicted set of coordinates and a ground-truth set of coordinates associated with the predicted set of coordinates, and (b) at least one second loss function configured to determine at least one rotational difference between the predicted set of coordinates and the ground-truth set of coordinates. The code also causes the one or more processors to train a generalized machine learning model to predict geometric information of an unseen protein-ligand structure based on the at least one adjustment.

In an embodiment, a method includes receiving, at a processor, a first indication associated with a first protein molecule and a second indication associated with a first ligand molecule. The method also includes predicting, via the first processor and using a machine learning model, three-dimensional coordinates associated with a first protein-ligand structure that includes the first protein molecule and the first ligand molecule, the machine learning model including a plurality of weights that are based on (1) a first error associated with a predicted position of a ligand atom included in a second ligand molecule from a second protein-ligand structure, the predicted position of the ligand atom being relative to a predicted position of an alpha-carbon protein atom included in a second protein molecule from the second protein-ligand structure, and (2) a second error associated with a predicted position of the alpha-carbon protein atom relative to a predicted position of a ligand atom included in the second ligand molecule.

In an embodiment, a method includes receiving, at a processor, a first indication associated with a first protein molecule and a second indication associated with a first ligand molecule. The method also includes predicting, via the first processor and using a machine learning model, three-dimensional coordinates associated with a first protein-ligand structure that includes the first protein molecule and the first ligand molecule, the machine learning model including a plurality of weights that are based on (1) a first error associated with a predicted position of a ligand atom included in a second ligand molecule from a second protein-ligand structure, the predicted position of the ligand atom being relative to a predicted position of an alpha-carbon protein atom included in a second protein molecule from the second protein-ligand structure, and (2) a second error associated with a predicted position of the alpha-carbon protein atom relative to a predicted position of a ligand atom included in the second ligand molecule.

In some implementations, the plurality of weights can be based further on a third error associated with a predicted position of a sidechain protein atom included in the second protein molecule, the predicted position of the sidechain protein atom being relative to the predicted position of the ligand atom. In some implementations the predicted position of the ligand atom can be a first predicted position, and the plurality of weights can be based further on a third error associated with a second predicted position of the ligand atom relative to a predicted position of a sidechain protein atom included in the second protein molecule. In some implementations, the ligand atom can be bonded to two additional ligand atoms and is a central ligand atom. In some implementations, the first error can be iteratively determined based on each alpha-carbon protein atom from a plurality of alpha-carbon protein atoms included in the second protein molecule. Additionally, the second error can be iteratively determined based on each central ligand atom from a plurality of central ligand atoms included in the second ligand molecule.

DETAILED DESCRIPTION

One or more embodiments of the present disclosure include a neural network for a protein-ligand (P-L) co-folding engine that learns a ligand binding site, its geometry and how the structure of a protein changes in the presence of a bound ligand. The neural network can also be used to expedite the hit discovery process in drug discovery programs. Given a protein-ligand structure, protein-ligand docking can be used to find the optimal (or near optimal) binding between a ligand and a protein. Protein-ligand (P-L) docking is a molecular modelling technique used to predict the structure in which a ligand interacts with a protein. This technique can involve the modelling of a protein chain and a ligand (such as a small molecule). The conformation of this P-L complex can be established for example through X-ray crystallography, NMR, or CryoEM with varying amounts of noise and accuracy depending on the experimental technique used. Identification of a binding site, where a ligand is bound to a protein, is used to launch virtual screening (VS) campaigns as the physical shape. Additionally, the electrostatic environment of the binding site is used to form interactions with ligands.

In some embodiments, the protein-ligand co-folding engine uses deep learning to predict protein-ligand complex structures. In some implementations, the protein-ligand co-folding engine can (1) use a deep learning model to predict joint protein-ligand molecular graphs based on input distograms of protein molecule atoms that are invariant to rotations and translation in a three-dimensional (3D) space, (2) extend the definition of a predicted 3D protein node frame to ligand atoms based on a structural loss such as Frame-Aligned Point Error (FAPE) loss, (3) adopt the use of ligand conformation losses and overcome problems with inherent ligand symmetries, and (4) devise a model training procedure(s) involving a random selection of protein backbone atoms to ensure a high level of model generalization to unseen proteins and/or unseen protein-ligand structures.

Figure 1:
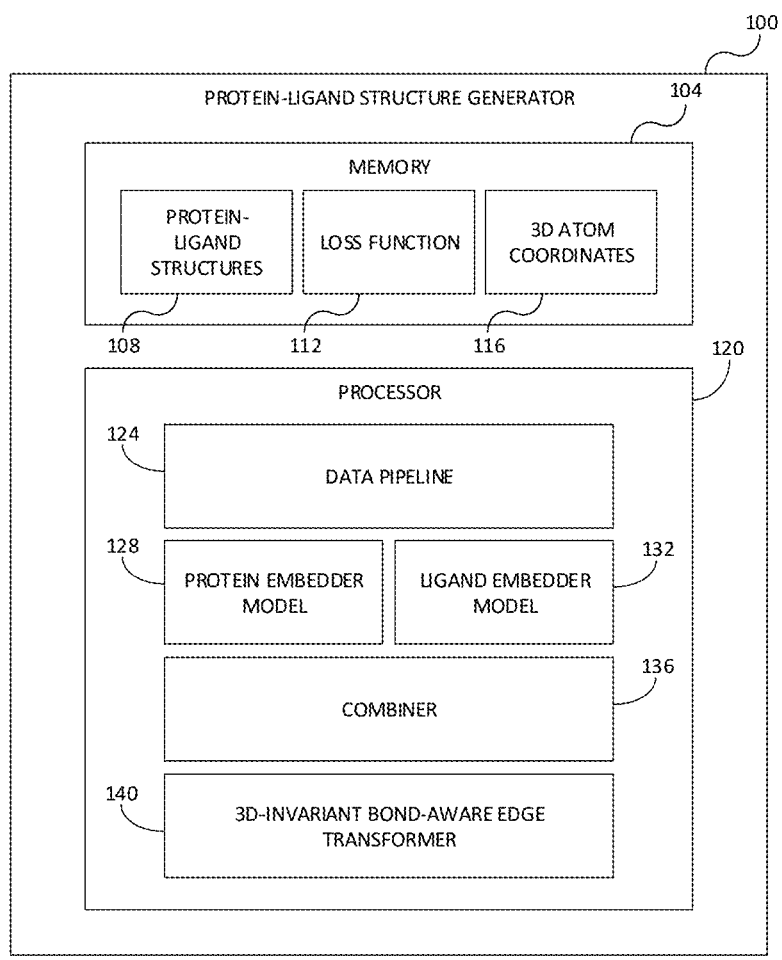
FIG. 1 is a diagrammatic illustration of a protein-ligand structure generator using deep learning, according to an embodiment.

FIG. 1 is a diagrammatic illustration of a protein-ligand structure generator 100 using deep learning, according to an embodiment. The protein-ligand structure generator 100 can also be referred to as a "protein-ligand co-folding engine." The protein-ligand structure generator 100 can be or include a hardware-based computing device, such as, for example, a computer, a server, a cluster of servers, a desktop, a laptop, a smartphone, and/or the like. The protein-ligand structure generator 100 includes a memory 104 operatively coupled to a processor 120, where the memory 104 stores instructions to be executed by the processor 120. The memory 104 and the processor 120 can communicate with each other, and with other components, via a bus (not shown). The bus can include any of several types of bus structures including a memory bus, a memory controller, a peripheral bus, a local bus, and any combinations thereof, using any of a variety of bus architectures.

The processor 120 can be or include, for example, a hardware-based integrated circuit (IC), or any other suitable processing device configured to run and/or execute a set of instructions or code. For example, the processor 120 can be a general-purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC) and/or the like. In some implementations, the processor 120 can be configured to run any of the methods and/or portions of methods discussed herein.

The memory 104 can be or include, for example, a random-access memory (RAM), a memory buffer, a hard drive, a read-only memory (ROM), an erasable programmable read-only memory (EPROM), and/or the like. In some instances, the memory 104 can store, for example, one or more software programs and/or code that can include instructions to cause the processor 120 to perform one or more processes, functions, and/or the like. In some implementations, the memory 104 can include extendable storage units that can be added and used incrementally. In some implementations, the memory 104 can be a portable memory (e.g., a flash drive, a portable hard disk, and/or the like) that can be operatively coupled to the processor 120. In some instances, the memory 104 can be remotely operatively coupled with the protein-ligand structure generator 100, where the protein-ligand structure generator 100 can include a remote database device. The memory 104 can be or include, for example, a hard disk drive, a magnetic disk drive, an optical disc drive in combination with an optical medium, a solid-state memory device, and any combinations thereof. In some implementations, the storage device can be removably interfaced with the protein-ligand structure generator 100 (e.g., via an external port connector; not shown). In some implementations, the memory 104 can include an associated machine-readable medium that can provide non-volatile and/or volatile storage of machine-readable instructions, data structures, program modules, and/or other data for the protein-ligand structure generator 100. In some cases, the protein-ligand structure generator 100 can include software that can reside, completely or partially, within the machine-readable medium and/or the processor 120.

The protein-ligand structure generator 100 can also include a communication interface (not shown). The communication interface can be a hardware component of the protein-ligand structure generator 100 to facilitate data communication between the protein-ligand structure generator 100 and external devices (e.g., a network, a compute device, a server, etc.; not shown). The communication interface can be operatively coupled to and used by the processor 120 and/or the memory 104. The communication interface can be, for example, a network interface card (NIC), a Wi-Fi® module, a Bluetooth® module, an optical communication module, and/or any other suitable wired and/or wireless communication interface.

The protein-ligand structure generator 100 can store multiple protein-ligand structures 108, representations of multiple loss functions 112 (e.g., in text or code), and 3D atom coordinates 116 in the memory 104.

In some instances, a protein-ligand structure of multiple protein-ligand structures 108 can include a complex of a protein bound with a ligand that is formed following molecular recognition between proteins that interact with each other or with various other molecules. The ligand can be defined as any molecule or atom that irreversibly binds to a receiving protein molecule, otherwise known as a receptor. The protein-ligand structure can include, for example, one-dimensional (1D) protein sequences and two-dimensional (2D) ligand structures. The loss functions 112 can include software methods and/or processes of evaluating one or more neural networks and/or machine learning models, such as a 3D-invariant bond-aware edge transformer 140 of the protein-ligand structure generator 100. For instance, the loss functions 112 can output higher or lower values that indicate the accuracy and/or performance of the 3D-invariant bond-aware edge transformer 140 in generating a predicted 3D protein-ligand structure and its 3D atom coordinates 116 (e.g., a spatial representation). For example, the loss functions 112 can specify a penalty for an incorrect prediction by the 3D-invariant bond-aware edge transformer 140 based on a comparison between the predicted 3D protein-ligand structure and what the actual (e.g., ground-truth) 3D protein-ligand structure is supposed to be. Based on this penalty, the 3D-invariant bond-aware edge transformer 140 can be configured to determine at least one adjustment to the 3D atom coordinates 116. At least one weight included in the neural network(s)/machine-learning model(s) can be based on the at least one adjustment. In some cases, the loss functions 112 can include a simple binary value indicating the accuracy of the predicted 3D protein-ligand structure within some threshold and/or range.

In some implementations, the loss functions 112 used to train the one or more neural networks and/or machine learning models to output predicted 3D protein-ligand structures can include at least one of (1) a Frame Aligned Point Error (FAPE) function applied to the training of a neural network associated a protein molecule, (2) a torsion loss function applied to the training of the neural network associated with the protein molecule, (3) a Frame Aligned Point Error (FAPE) function applied to the training of the neural network associated with a ligand molecule, (4) a dihedral and angle loss function applied to the training of the neural network associated with the ligand molecule, or (5) a loss function based on a N-hop distance associated with a degree of separation in a molecular two-dimensional (2D) graph representation of the ligand molecule. The 3D atom coordinates 116 can include, for example, predicted coordinates of 3D protein-ligand complex structures. In some cases, the memory 104 can also store geometric information including 3D atom coordinates 116 of a plurality of atoms in the form of a distogram, where the geometric information can be obtained from intermediate model predictions. In some cases, the distogram can be determined at least partially provided a priori, where the partially provided a priori determination includes predicted geometric information of a co-folding structure of a future protein and ligand molecules including 3D atom coordinates 116 of the co-folding structure. The processor 120 of the protein-ligand structure generator 100 can include a data pipeline 124 that parses protein-ligand structures 108 into input data for the protein embedder model 128 and/or the ligand embedder model 132. The memory 104 can store instructions to cause the processor 120 to convert, via the data pipeline 124, the protein-ligand structure from into input data including protein amino-acid sequence, a simplified molecular-input line-entry system (SMILES) string representing a ligand molecule, and/or initial coordinates for atoms of the predicted geometric information including 3D coordinates of a co-folding structure of a second protein molecule and a second ligand molecule. In some implementations, the input data can also be converted to any other molecular representation, such as, for example, self-referencing embedded strings (SELFIES). The data pipeline 124 can be further described in FIG. 2.

The protein embedder model 128 and/or the ligand embedder model 132 can include a neural network and/or a machine learning model. The protein embedder model 128 generates a first plurality of feature vectors based on training protein data (e.g., ground-truth data) associated with a plurality of atoms of a first protein molecule. A protein molecule can also be referred to as a "protein." The plurality of atoms of the first protein molecule and/or any protein molecule can also be referred to as "protein atoms." The first protein molecule and/or any protein molecule can include a linear protein sequence. For example, a primary structure of a protein includes a linear sequence of amino acids, where the protein is built from a set of amino acids having different chemistries. Multiple linear sequences can be inputted into the protein embedder model 128 to generate the first plurality of feature vectors. The first plurality of feature vectors can include initial coordinates of the first protein molecule in a graphical and/or distogram form.

The first plurality of feature vectors can also be referred to as "protein embeddings," "representation of protein embeddings," or "protein features." In some implementations, the training protein data can include previously-predicted geometric information of co-folding structures of previous protein molecule and ligand molecules. The training protein data can also include actual protein-ligand structures correlated to previously-generated feature vectors of protein molecules, previously-generated 3D coordinates of proteins, and/or the like. In some implementations, the training protein data (e.g., ground-truth data) for the first protein molecule can include an amino acid sequence and/or not include a 3D structure of the first protein.

The ligand embedder model 132 generates a second plurality of feature vectors based on training ligand data associated with a plurality of atoms of a first ligand molecule. A ligand molecule can also be referred to as a "ligand." The plurality of atoms of the first ligand molecule and/or any ligand molecule can also be referred to as "ligand atoms." In coordination chemistry, a ligand can include, for example, an ion or molecule that binds to a central metal atom to form a coordination complex. The second plurality of feature vectors can also be referred to as "ligand embeddings," "representations of ligand embeddings," or "ligand features." The second plurality of feature vectors can include ligand structure such as a 2D ligand structure of the first ligand molecule and/or any ligand molecule. In some cases, the first ligand molecule can include a SMILES string representation of the first ligand molecule and/or any ligand molecule, where the ligand embedder model 132 transforms the SMILES string representation into a molecular graph with node representations including edges and nodes, where the nodes correspond to multiple atoms of the first ligand molecule and the edges correspond to chemical bond activities/connections between the atoms. In some implementations, the training ligand data can include previously-predicted geometric information of co-folding structures of previous protein molecule and ligand molecules. The training protein data can also include actual protein-ligand structures correlated to previously-generated feature vectors of ligand molecules, previously-generated 3D coordinates of ligands, and/or the like. In some implementations, the training ligand data for the first ligand molecule can also include representations of an atom structure of the first ligand molecule. In some cases, the training ligand data for the first ligand molecule do not include a 3D representation of the atom structure of the first ligand molecule.

The protein embedder model 128 and the ligand embedder model 132 can extract features from the first protein molecule and the first ligand molecule, where the featurization can be executed independently for the first protein molecule and the first ligand molecule and/or in parallel. In some implementations, for a protein representation, the protein-ligand structure generator 100 and/or the protein embedder model 128 can use alpha-carbon ("C-alpha") coordinates, sidechain torsion angles, and/or pretrained embeddings.

In some implementations, the protein embedder model 128 can include a pretrained model to produce the first plurality of feature vectors including protein embeddings, where the representation of the protein embeddings can contain a rich representation of the protein structure defined locally for each amino acid of the protein-ligand structure. In some implementations, the protein embedder model 128 can use linear embedding to reduce the dimensional projection of protein embeddings of the first protein molecule to generate the first plurality of feature vectors including representations of protein embeddings. In some implementations, the protein embedder model 128 can perform a linear projection of the first protein molecule to generate the protein embeddings with a hidden dimension for the 3D-invariant bond-aware edge transformer 140. In some implementations, the protein embedder model 128 can embed the residues associated with protein atoms (e.g. the plurality of atoms of the first protein molecule) to generate the first plurality of feature vectors, where the first plurality of feature vectors can include:: $\{f_i^{res}\}$, $1 \leq i \leq N_{res}$, where N is a node. In some cases, the residues are associated with alpha-carbon protein atoms from the plurality of protein atoms of the first protein molecule. The 3D-invariant bond-aware edge transformer 140 can receive an input including the plurality of atoms of the first molecule in the form of a distogram, where the input is invariant to rotations and translation in a 3D space. The input for the 3D-invariant bond-aware edge transformer 140 can also be invariant to rotations and translations in supervision of the 3D-invariant bond-aware edge transformer 140 through the loss functions 112.

The ligand embedder model 132 generates, based on training ligand data of a first ligand molecule, a second plurality of feature vectors associated with a plurality of atoms of the first ligand molecule. In some implementations, the ligand embedder model 132 projects ligand features of the second plurality of feature vectors via concatenation of 1-hot encoding of chemical features into the hidden dimension of the 3D-invariant bond-aware edge transformer 140 by a standard linear layer. The ligand embedder model 132 can also to reduce the dimensional projection of ligand features of the first ligand molecule to generate the second plurality of feature vectors including representations of ligand embeddings. In some implementations, the ligand embedder model 132 uses pair representation for the ligand of the input data, where the ligand includes linear embeddings (into the hidden dimension of the 3D-invariant bond-aware edge transformer 140) of the k-hop adjacency matrix with k=3.

In some implementations, generating the second plurality of feature vectors includes embedding a plurality of features of an atom from the plurality of atoms of the first ligand molecule into a feature vector from the second plurality of feature vectors. The plurality of features of the atom can be associated with for example (1) an aromaticity of the atom, (2) a molecular mass of the atom, (3) an atom type of the atom, (4) valence of the atom in the first ligand molecule, (5) an electronic charge of the atom, (6) stereo-chemistry of the atom around tetrahedral centers, (7) a number of hydrogen atoms connected to the atom, and/or (8) a hybridization of the atom. In some cases, the features can also include features such as a SMILES string defining the first ligand molecule, where the string can be transformed into a molecular graph with $N_{lig}$ nodes corresponding to atoms, and edges corresponding to chemical bonds between atoms. Each node can be attributed to a 44-dimensional feature vector. The dimensional feature vector can include, for example, the concatenation of a binary encoding of the aromaticity of the atom, the molecular mass of the atom scaled by a parameter, and 1-hot encodings, which include the atom type, valence of the atom in the molecule (counting Hydrogens), the formal charge of the atom, the stereochemistry of the atom around tetrahedral centers, the number of Hydrogens attached to the atom, and/or the hybridization of the atom. In some implementations, the ligand embedder model 132 embeds the features into a ligand node features: $\{f_i^{lig}\}$, $1 \leq i \leq N_{lig}$ of the same dimensionality as $\{f_i^{res}\}$.

The protein-ligand structure generator 100 can also include a combiner 136. The combiner 136 can include, for example, any hardware/software used to combine protein information and ligand information. For example, the memory 104 can store instructions to cause the processor 120 to combine the first plurality of feature vectors (e.g. protein embeddings) and the second plurality of feature vectors (e.g. ligand embeddings) to generate via, the combiner 136, node representations of input data. The combiner 136 combines protein information and ligand information in the node representations including a single complex graph of $N=N_{res}+N_{lig}$ nodes. Node representations can include for example complex node features that are concatenated protein and ligand node representations:

$$f_i = \begin{cases} f_i^{res}, & 1 \leq i \leq N_{res} \\ f_{i-N_{res}}^{lig}, & N_{res} < i \leq N \end{cases}$$

The memory 104 stores instructions to further cause the processor 120 to generate, at the processor 120 and based on the training ligand data, a third plurality of feature vectors associated with a plurality of chemical bonds between atoms from the plurality of atoms of the first ligand molecule, where the third plurality of feature vectors are edge representations of the input data. The third plurality of feature vectors can include edge representations of the second plurality of feature vectors (e.g. representation of ligand embeddings). For instance, the processor 120 can use linear embedding of the ligand features from the second plurality of feature vectors to produce the third plurality of feature vectors including ligand edge representations: $\{e_{ij}^{lig}\}$, $1 \leq i$, $j \leq N_{lig}$.

In some implementations, generating the third plurality of feature vectors includes embedding a plurality of features of a chemical bond from the plurality of chemical bonds into a feature vector from the third plurality of feature vectors. The plurality of features of the chemical bond can be associated with for example (1) stereo-chemistry of atoms of the chemical bond around tetrahedral centers, (2) multiplicity of the chemical bond, (3) aromaticity of the chemical bond, (4) conjugation of the chemical bond, (5) rotatability of the chemical bond, and/or (6) whether the chemical bond is associated with a ring. In some implementations, the edges corresponding to chemical bonds between atoms can be attributed to a 13-dimension feature vector, which is for example the concatenation of a 1-hot encodings of the stereochemistry of the atom around tetrahedral centers, the multiplicity of the bond and binary flags for properties of the bond, such as aromaticity, conjugation, within a ring, and/or rotatability. In some cases, the third plurality of feature vectors (e.g., edge representations) can form a zero-padded padded tensor:

$$e_{ij} = \begin{cases} e_{i-}^{lig}, & 1 \le i \le N_{res} \\ f_{i-N_{res}}^{lig}, & N_{res} < i \le N \end{cases}$$

The protein-ligand structure generator 100 further includes the 3D-invariant bond-aware edge transformer 140. The 3D-invariant bond-aware edge transformer 140 is software and/or hardware that transforms the single complex graph of $N=N_{res}+N_{lig}$ including protein and ligand information (e.g., node representations, edge representations, protein residues, or the like) into an updated complex graph, where the complex graph can be updated in multiple iterations. In some cases, the 3D-invariant bond-aware edge transformer 140 can generate the geometric information for protein molecules and ligand molecules. The 3D-invariant bond-aware edge transformer 140 can also be referred to as a "neural network" or "machine learning model." For instance, the 3D-invariant bond-aware edge transformer 140 can generate geometric information of a co-folding structure of a second protein molecule and a second ligand molecule, the geometric information including (3D) coordinates of the co-folding structure based on the geometric information of a co-folding structure of the first protein molecule and the first ligand molecule. In other words, the output of the 3D-invariant bond-aware edge transformer 140 is geometric information encoded in frames (representing rotations) and 3D coordinates for each of the modelled atoms in the complex of the co-folding structure. The output geometric information can include a predicted 3D protein-ligand structure and/or 3D protein-ligand co-folding structure.

The protein embedder model 128 and the ligand embedder model 132 can also be trained to produce a trained protein embedder model and a trained ligand embedder model. For instance, the trained protein embedder model can be trained to generate another plurality of feature vectors of another protein molecule. The trained ligand embedder model can be trained to generate another plurality of feature vectors of another ligand molecule. Alternatively or additionally, the protein-ligand structure generator 100 can include another neural network such as a second neural network different from a first neural network being the 3D-invariant bond-aware edge transformer 140 to better predict geometric information of co-folding structures including 3D protein-ligand structures and their 3D atom coordinates.

The memory 104 stores instructions to further cause the processor 120 to train the neural network using (1) the input data including the node representations and the edge representations and (2) the loss functions 112, to generate a trained neural network to predict geometric information of the co-folding structure of a second protein molecule and a second ligand molecule, where the geometric information includes 3D coordinates of the co-folding structure. In some cases, training the neural network further includes using coordinates of the plurality of atoms of the first protein molecule, in the form of a distogram. For instance, the coordinates of the plurality of atoms $\{\vec{x}_i^{init}\}$, $1 \le i \le N$ can be used for training the neural network where the distogram form includes:

$$d_{ij}^{init} = \|\vec{x}_i^{init} - \vec{x}_j^{init}\|_2, 1 \le i,j \le N$$

In some cases, the coordinates may come from for example black hole (uninformative, zero) initialization for co-folding, true protein structure for re-docking, the apoprotein or holoprotein structure of the protein from a different experiment (and different ligand) in a Protein Data Bank (PDB) for cross-docking.

The neural network can include a process (or method) to maintain and jointly update the node representations $\{s_i\}$, $1 \le i \le N$ and edge representations $\{z_{ij}\}$, $1 \le i, j \le N$ of the geometric information of the co-folding structure of the first protein molecule and the first ligand molecule for all atoms in the graph as a result of the combining of protein and ligand information. Such a process for the neural network and/or the protein-ligand structure generator 100 can include for example:

---
Process 1: Protein-ligand structure generator
---
Require: Complex node features $\{f_i\}$, edge features $\{e_{ij}\}$, and the initial distogram $\{d_{ij}^{int}\}$
1:   $s_i^{prev}, z_i^{prev}, d_i^{prev} \leftarrow 0,0,0$
2:   Choose the number of recycling iterations T from $\{1,2,3,4\}$
3:   for $t \in [1, T]$ do
4:      $z_{ij} \leftarrow e_{ij} + f_i + f_j + \text{Linear}(d_{ij}^{int}) + \text{Linear}(d_{ij}^{prev}) + \text{LayerNorm}(z_{ij}^{prev})$
5:      $s_i \leftarrow \text{LayerNorm}(f_i) + \text{LayerNorm}(f_i^{prev})$
6:      $\{s_i\}, \{z_{ij}\} \leftarrow \text{GraphEncoder}(\{s_i\}, \{z_{ij}\})$
7:      $\vec{x}_i \leftarrow \text{Linear}(s_i)$
8:      $s_i^{prev}, z_i^{prev}, d_i^{prev} \leftarrow s_i, z_{ij}, \|\vec{x}_i - \vec{x}_j\|_2$
9:   end for
10: return $\{s_i\}$

---

The neural network can employ, for example, a 48-layer neural network that operates with multiple-sequence alignment (MSA) representation containing multiple residue representations corresponding to different biological species. In alternative implementations, instead of operating with MSA, the protein-ligand structure generator 100 can model only human protein sequences and append the ligand atom representations to the protein residue representations. The neural network can, for example, perform a random number of iterative updates to the node representations $\{s_i\}$ and/or the edge representations $\{z_{ij}\}$, and truncate backpropagation of gradients between the iterations (recycling). Between these iterations, the neural network can decode the intermediate geometric predictions from the machine learning model (e.g., the 3D-invariant bond-aware edge transformer 140) and embed them into complex representations so the neural network can learn to correct its past predictions. In some cases, the number of iterations is randomly sampled between 1 and 4, where only the latest iteration is directly supervised. In some cases, the input for the 3D-invariant bond-aware edge transformer 140 can also be invariant to rotations and translations in supervision of the 3D-invariant bond-aware edge transformer 140 through the loss functions 112.

The neural network generates, for example, the trained neural network that predicts geometric information of the co-folding structure of the second protein molecule and a second ligand molecule, the geometric information including 3D coordinates of the co-folding structure. The geometric information can be encoded in frames representing rotations and coordinates for each of the modelled atoms of the co-folding structure in. In some implementations, the neural network follows a typical definition of backbone frames and predict $C_\alpha$ frames $\{T_i\}$ and coordinates $\{\vec{x}_i\}$ from the corresponding node representations $\{s_i\}$, $1 \leq i \leq N_{res}$. In some cases, the neural network predicts ligand atom coordinates from ligand node representations by considering all possible triplets of bonded ligand atoms to define frames of their predicted coordinates.

After an initial linear projection to the hidden dimension of the transformer, both protein and ligand representations are concatenated, effectively concatenating the ligand atoms to the $C_\alpha$ terminus of a protein residue. The protein-ligand structure generator 100 relies on the highly-expressive pairwise interactions between protein-ligand complex nodes by updating the pairwise interactions of the edge representations $\{z_{ij}\}$ and does not use Invariant Point Attention (IPA). Hence, the neural network and/or the protein-ligand structure generator 100 does not explicitly operate with the protein node frames and has access to the geometric information through the distogram $\{d_{ij}^{init}\}$ without accessing other information in the protein node frames. Alternatively or additionally, and in some implementations, the protein-ligand structure generator 100 can employ IPA layers with shared weights to cause the concatenated representations to go through a number of iterations of the IPA layers.

The protein-ligand structure generator 100 can train the neural network using a combination of loss functions 112 that are associated with the ligand and/or the protein. In some implementations, the loss functions 112 can include at least one of (1) a Frame-Aligned Point Error (FAPE) function applied to the training of the neural network associated with the first protein molecule (e.g., where protein-centric frames are centered on a protein atom), (2) a torsion loss function applied to the training of the neural network associated with the first protein molecule, (3) a Frame Aligned Point Error function applied to the training of the neural network associated with the first ligand molecule, (4) a dihedral and angle loss function applied to the training of the neural network associated with the first ligand molecule, and/or (5) a loss function based on a N-hop distance associated with a degree of separation in a molecular graph representation of the first ligand molecule.

The notation for loss functions includes $T^{true}$: the true frames for a given structure including both the translation and orientation: $T = (R, \vec{t})$, where $R \in SO(3)$ is the rotation matrix from the identity to the orientation and $\vec{t} \in \mathbb{R}^3$ is the translation vector, $T^{pred}$ is the predicted frames for a given structure, and $T^{global}$ is the global Euclidean transform between two rigid bodies $A, B \in \mathbb{R}^{N \times 3}$ in practice derived by the Kabsch algorithm used to minimize the root-mean-square deviation (RMSD) between them. The FAPE function applied to the training of the neural network associated with the first protein molecule can follow:

$$FAPE\left(\{T_i^{true}\}, \{\vec{x}_j^{true}\}, \{T_i^{pred}\}, \{\vec{x}_j^{pred}\}, v\right) \stackrel{def}{=}$$

-continued
$$\frac{1}{N_{frames} N_{points}} \sum_{ij} \min\left\{c, \left\|T_i^{true}(\vec{x}_j^{true}) - T_i^{pred}(\vec{x}_j^{pred})\right\|\right\}$$

where c is a clamping constant. The memory 104 stores instructions to cause the processor 120 to decouple the frames and rotations so that the loss for an arbitrary number of frames is computed among another number of translations. All translations including both the protein and ligand translations, for example, can be considered in the FAPE function. In some cases, the only frames used in the FAPE function can include secondary protein amino acids (protein AAs). In some instances, the FAPE function can use frames centered on backbone protein atoms (e.g., alpha-carbon atoms) and/or sidechain protein atoms. For example, the FAPE function can be configured to generate a predicted position of a ligand atom relative to a frame centered (or substantially centered) based on a position of a predicted position of an alpha-carbon protein atom and/or a sidechain protein atom. A loss associated with the FAPE function can be generated based on a comparison between the predicted position of the ligand atom and a ground-truth position of the ligand atom (e.g., based on ground-truth frames centered at ground-truth positions of alpha-carbon protein atoms and/or sidechain protein atoms).

The torsion loss function applied to the training of the neural network associated with the first protein molecule can be applied using a similar approach to the setup above, where the approach includes performs an L2 norm on the unit circle plus an extra loss on the vector norm to keep gradients stable. To account for symmetric sidechain atoms, the memory 104 can store instructions to cause the processor 120 to calculate the minimum of the loss and its symmetric counterpart. For example, the protein-ligand structure generator 100 can extend the number of symmetric sidechain atoms to include the last two nitrogen atoms from arginine. The torsion loss function can follow:

$$\vec{X}_{norm}^{pred} = \frac{\vec{X}^{pred}}{\|\vec{X}^{pred}\|} \ell_{torsion}\left(\vec{X}^{true}, \vec{X}^{pred}\right) =$$

$$\alpha \cdot \|\vec{X}^{pred}\| + \min\left\{\left\|\vec{X}^{true} - \vec{X}_{norm}^{pred}\right\|_2^2, \left\|\vec{X}^{true} - \vec{X}_{norm}^{pred+}\right\|_2^2\right\}$$

Where $\vec{X}^{true}, \vec{X}^{pred} \in \mathbb{R}^2$ encoding angles in the format of (cos X, sin X) as points in the unit circle, $\alpha$ is a small constant ($\alpha=0.02$) intended to keep the predicted values close to the unit circle and stabilize training dynamics as very small, predicted values could cause noisy gradient signals to the model, and $\vec{X}^{pred+}$ is the symmetric torsion where applicable. Table 1 includes symmetric atoms with ambiguous names:

TABLE 1

Symmetric atoms with ambiguous names

| Aminoacid Code | Atom Codes |
|---|---|
| ASP | $O^{\delta 1} \leftrightarrow O^{\delta 2}$ |
| GLU | $O^{\epsilon 1} \leftrightarrow O^{\epsilon 2}$ |
| PHE | $C^{\delta 1} \leftrightarrow C^{\delta 2}, C^{\epsilon 1} \leftrightarrow C^{\epsilon 2}$ |
| TYR | $C^{\delta 1} \leftrightarrow C^{\delta 2}, C^{\epsilon 1} \leftrightarrow C^{\epsilon 2}$ |
| ARG | $N^{\eta 1} \leftrightarrow N^{\eta 2}$ |

The FAPE function applied to the training of the neural network associated with the first ligand molecule can be used to detach frames and translations using the formulation of the FAPE function applied to the training of the neural network associated with the first protein molecule described above. The protein-ligand structure generator 100 can ignore the nature of ligand atoms and the non-trivial definition of frames by considering all possible triplets without repetitions that can be defined on the ligand molecular graph. In some implementations, a triplet includes a central atom and two other atoms bonded to it. The protein-ligand structure generator 100 can build both the predicted and the true frames from the corresponding predicted and true translations of the building atoms, using the graph connectivity for the molecule. The protein-ligand structure generator 100 can center the frame at the central atom of the triplet, and obtain axes from by a Gram-Schmidt process. Hence, as in the protein case, all translations are considered here, both the protein and the ligand translations, although the only frames used are frames (e.g., ligand-centric frames) corresponding to (e.g., centered based on) a ligand. For example, the FAPE function can be configured to generate a predicted position of a protein atom (e.g., an alpha-carbon protein atom and/or a sidechain protein atom) relative to a frame centered (or substantially centered) based on a position of a predicted position of ligand atom (e.g., a central ligand atom). A loss associated with the FAPE function can be generated based on a comparison between the predicted position of the protein atom and a ground-truth position of the protein atom (e.g., based on ground-truth frames centered at ground-truth positions of central ligand atoms).

At least one loss (e.g., a ligand-only loss) can be associated with the first ligand molecule. For example, the dihedral and angle loss function applied to the training of the neural network associated with the first ligand molecule can maximize a von Mises dihedral angle log-likelihood function in closed form, the dihedral and angle loss function including:

$$\mathcal{L}_{angle} \stackrel{def}{=} \frac{1}{\#E_3} \sum_{(u,v,w)\in E_4} \cos\left(L^{true}(\vec{vu}, \vec{vw}) - L^{pred}(\vec{vu}, \vec{vw})\right)$$

$$\mathcal{L}_{dihedral} \stackrel{def}{=} \frac{1}{\#E_4} \sum_{\#(u,v,wx)\in E_4} \cos\left(L^{true}(\vec{n}_{uvw}, \vec{n}_{vwx}) - L^{pred}(\vec{n}_{uvw}, \vec{n}_{vwx})\right)$$

where $E_3=\{(u, v, w)|(u, v), (v, w)\in E\}$ and $E_4=\{(u, v, w, x)|(u, v), (v, w), (w, x)\in E\}$ are all paths in the molecular graph of length 3 and 4 respectively, and $\vec{n}_{uvw}$ is the unit normal vector to the plane containing u, v, w. In other words, $\mathcal{L}_{angle}$ tries to get angles between bonds correct, while $\mathcal{L}_{dihedral}$ tries to get bond torsions correct.

The N-hop loss function based on a N-hop distance associated with the degree of separation in the molecular graph representation of the first ligand molecule can be applied to ensure physical plausibility of generated conformers. In some implementations, the protein-ligand structure generator 100 can include a loss on the N-hop distance, where n represents the degree of separation in the molecular graph (2D). The protein-ligand structure generator 100 can implement the loss as an absolute error with respect to the true distances found in the ground-truth ligand conformer. The N-lop loss function follows:

$$\mathcal{L}_{angle} = \sum_{d_{graph}(i,j)=n} |d_{ij}^{pred} - d_{ij}^{true}|$$

where $d_{graph}(i, j)$ is the length of the shortest path i↔j in the molecular graph of the ligand, and $d_{ij}=\|x_i-x_j\|_2$ are the predicted or true distograms.

In some implementations, the memory 104 can store instructions to further cause the processor 120 to train the neural network using coordinates of the plurality of atoms of the first ligand molecule. Training can further include re-calculating the coordinates of the plurality of atoms of the first ligand molecule, based on a loss function from the loss functions 112, to consider automorphism of a set of atoms from the plurality of atoms of the first ligand molecule. In some instances, training the neural network includes iteratively re-training the neural network using an output from a previous training of the neural network to generate the trained neural network.

In some cases, ligands can contain pairs of chemically equivalent atoms. Examples of such cases are carbon atoms in benzene rings, dimethyl radicals or symmetric esters. This may lead to some chemically plausible conformations being unfairly penalized only because of atom numbering differing from the ground truth. To mitigate this, the protein-ligand structure generator 100 can employ automorphisms of the ligand's molecular graph, which are permutations (relabellings) σ of its atoms such that i, σ(i) have the same type and stereochemistry, and bond types between i, j and between σ(i), σ(j) are the same. In some implementations, prior to calculating the plurality of loss functions 112, the memory 104 can store instructions to cause the processor 120 to select a particular ligand loss $\mathcal{L}_{rename}$ and consider up to 8 automorphisms for every molecule at training time for which the processor 120 calculates the $\mathcal{L}_{rename}$, and pick the one with the smallest value. In some implementations, the ground truth can be relabeled to the best automorphism and use the renamed coordinates for the loss computation in for example the following process for ligand coordinate renaming:

---

Process 2: Ligand coordinate renaming

Require: Ligand true coordinates $\{x_i^{true}\}$, ligand predicted coordinates $\{x_i^{true}\}$, ligand automorphisms $\{a\}$, auxiliary renaming loss $\mathcal{L}_{rename}$
1:   $\mathcal{L}_{min} \leftarrow +\infty$
2:   $x_i^{best} \leftarrow 0$
3:   for t ∈ [1, K] do
4:     $\{x_i^{true,renamed}\} \leftarrow$ RenameWithAutomorphism($\{x_i^{true}\}$, $a_k$)
5:     $\mathcal{L} \leftarrow |\mathcal{L}_{rename} \{x_i^{renamed}\}, \{x_i^{true,renamed}\})$
6:     if $\mathcal{L} \leftarrow \mathcal{L}_{min}$, then
7:       $\mathcal{L}_{min} \leftarrow \mathcal{L}$
8:       $x_i^{best} \leftarrow x_i^{true,renamed}$
9:     end if
10:   end for
11:   return $\{x_i^{best}\}$ In training the neural network, the protein-ligand structure generator 100 can use a PDBBind dataset. The PDBBind dataset can be retrieved from a PDBBind database containing a comprehensive collection of experimentally measured binding affinity data (Kd, Ki, and IC50) for protein-ligand complexes deposited in the Protein Data Bank (PDB). In some instances, the PDBBind dataset includes around 19.450 affinity-annotated protein-ligand complexes, curated from the PDB. In some implementations, the memory 104 stores instructions to cause the processor 120 to split the PDBBind dataset into training, validation, and testing sets.

In some implementations, the memory 104 can store instructions to cause the processor 120 to randomly sample 125 unique proteins with complexes discovered after 2019 (363 complexes), and exclude all complexes with those ligands from the training and validation sets. In some cases, many proteins in the PDBBind dataset are multimeric. The memory 104 stores instructions to cause the processor 120 to constrain the input data to include only one chain and one ligand. The memory 104 further stores instructions to cause the processor 120 to identify for example the most influential chain in terms of binding the ligand and/or the chain that constitutes the majority of the binding pocket by fast end-to-end learning on protein surfaces. For instance, the memory 104 further stores instructions to cause the processor 120 to randomly sample a set of points $\{x_i\}$, $1 \leq i \leq S$ (usually S=500) around ligand atom coordinates $\{x_j^{lig}\}$, $1 \leq i \leq N_{lig}$ and optimize it with respect to the following potential:

$$U(\{x_i\}; \{x_j^{lig}\}) = -\frac{1}{2} \sum_{i=0}^{s} \left( \sigma(x_i) \cdot \log \left( \sum_{j=0}^{N_{lig}} \exp\left(\frac{-\|x_i - x_j^{lig}\|}{r_j}\right) \right) - r \right)^2,$$

$$\sigma(x) = \sum_{j=-}^{N_{lig}} \frac{\exp(-\|x - x_j^{lig}\|) \cdot r_j}{\sum_{k=0}^{N_{lig}} \exp(-\|x - x_k^{lig}\|)}$$

where $r_k$ denotes the van der Waals (VdW) atomic radius (set to 1.5A by default for heavy atoms) and r=1.05. In some implementations, for the cross-docking task described above, the memory 104 stores instructions to cause the processor 120 to generate predicted protein-ligand structures 108 for each protein in the PDBBind using a protein SEQRES records (records containing a listing of consecutive chemical components covalently linked in a linear fashion to form a polymer). The protein-ligand structure generator 100 can apply the Kabsch algorithm mentioned above to align the predicted protein-ligand structures 108 to the crystal structures represented as full atom point clouds. In some implementations, the protein-ligand structure generator 100 is concerned only with the alignment of the binding pocket of the ligand. The memory 104 of the protein-ligand structure generator 100 stores instructions to cause the processor 120 to select the atoms that constitute the binding pocket, where the processor 120 first computes, via the 3D-invariant bond-aware edge transformer 140, the Euclidean distance between each $C_\alpha$ and the nearest ligand atom. The protein-ligand structure generator 100 aligns on the resolved residues that are under the median of the Euclidean distance.

In some implementations, the memory 104 stores instructions to cause the processor 120 to crop the first protein molecule to select the plurality of atoms of the first protein molecule by choosing a seed amino acid from the first protein molecule within a pre-determined distance from the first ligand molecule and selecting a set of residues spatially within a certain distance from the seed amino acid. The memory 104 of the protein-ligand structure generator 100 stores instructions to cause the processor 120 to employ a "pocket-centric" cropping strategy that first chooses a random seed amino acid within a certain cutoff from the ligand and selects a desired number of its spatially closest neighboring residues. In some instances, a cropping strategy ensures good generalization from small crops of 128 amino acids used in training to large crops of size 640 and covers over 95% of proteins in PDB.

Figure 2:
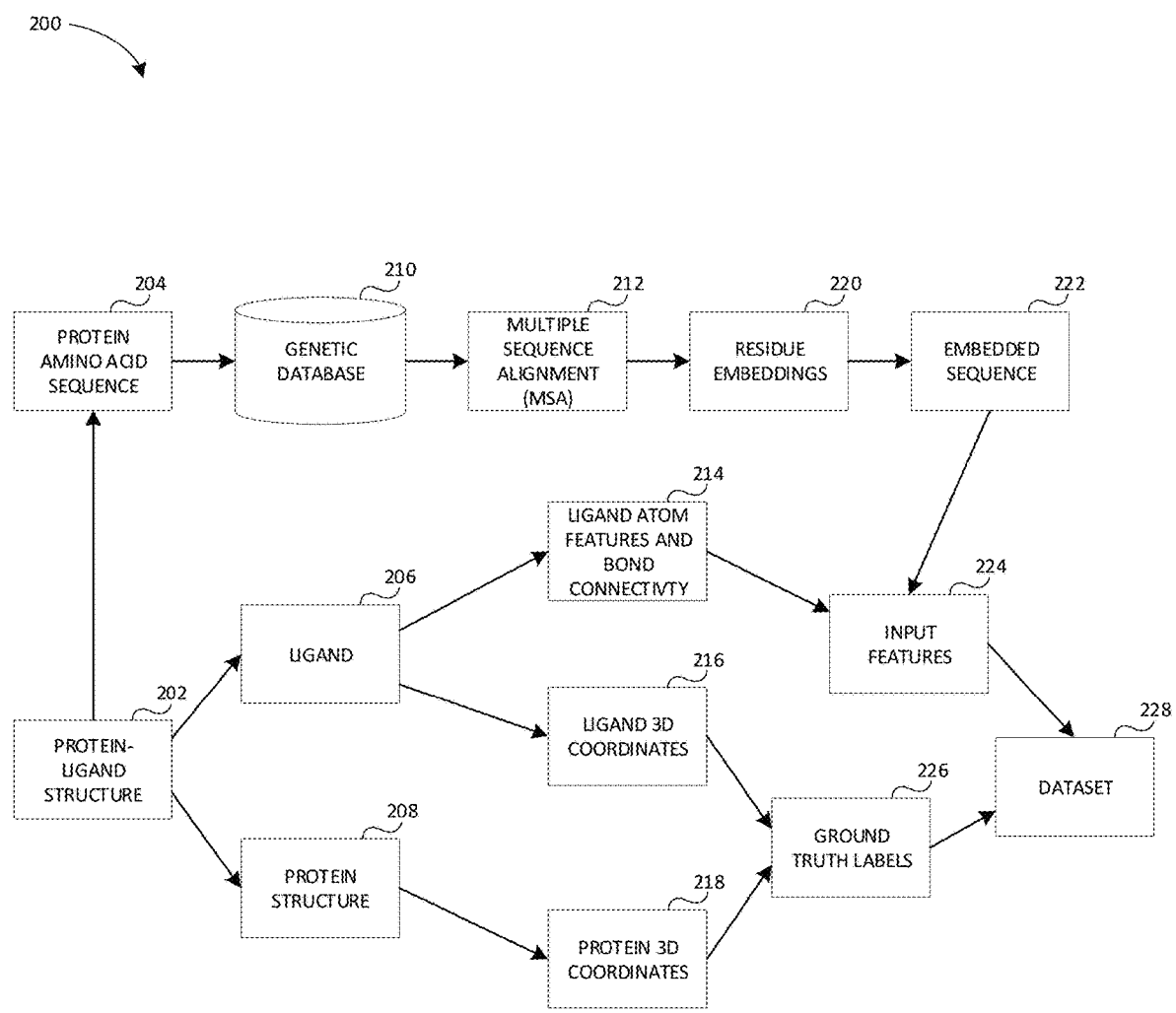
FIG. 2 is a flowchart of a system for a data pipeline for protein-ligand structure generation using deep learning, according to an embodiment.

FIG. 2 is a flowchart of a system for a data pipeline 200 for protein-ligand structure generation using deep learning, according to an embodiment. The data pipeline 200 can be similar to and/or consistent with the data pipeline 124 of FIG. 1. The data pipeline 200 can receive a representation of a protein-ligand structure 202 and extract it into a representation of a ligand 206 and a representation of a protein structure 208. The data pipeline 200 can also extract a representation of a protein amino acid sequence 204 from the protein-ligand structure 202.

The data pipeline 200 can then perform a lookup of a genetic database 210 based on the representation of protein amino acid sequence 204 to retrieve a multiple sequence alignment (MSA) 212 of a protein. In some implementations, the data pipeline 200 can further generate residue embeddings 220 of the representation of the protein amino acid sequence 204 based on the MSA 212, where the residue embeddings 220 are used to generate an embedded sequence 222.

In some implementations, the data pipeline 200 can also extract ligand atom features and bond connectivity 214 and a representation of the ligand 3D coordinates 216 of the representation of the ligand 206 from the protein-ligand structure 202. The data pipeline 200 can also extract a representation of a protein 3D coordinates 218 along with the representation of the ligand 3D coordinates 216, where both of them are used to generate ground truth labels 226 for evaluating and/or confirming protein-ligand complex graphs. The data pipeline 200 can further generate input features 224 based on the embedded sequence 222 and the ligand atom features and bond connectivity 214, where the input features can be used for example for the 3D-invariant bond-aware edge transformer of FIG. 1. In some cases, the data pipeline 200 can use an open source machine learning framework to generate a dataset 228 to train the neural network and/or the 3D-invariant bond-aware edge transformer described in FIG. 1. In some implementations, the dataset 228 can include the training protein dataset and/or the training ligand data set as described in FIG. 1.

Figure 3:
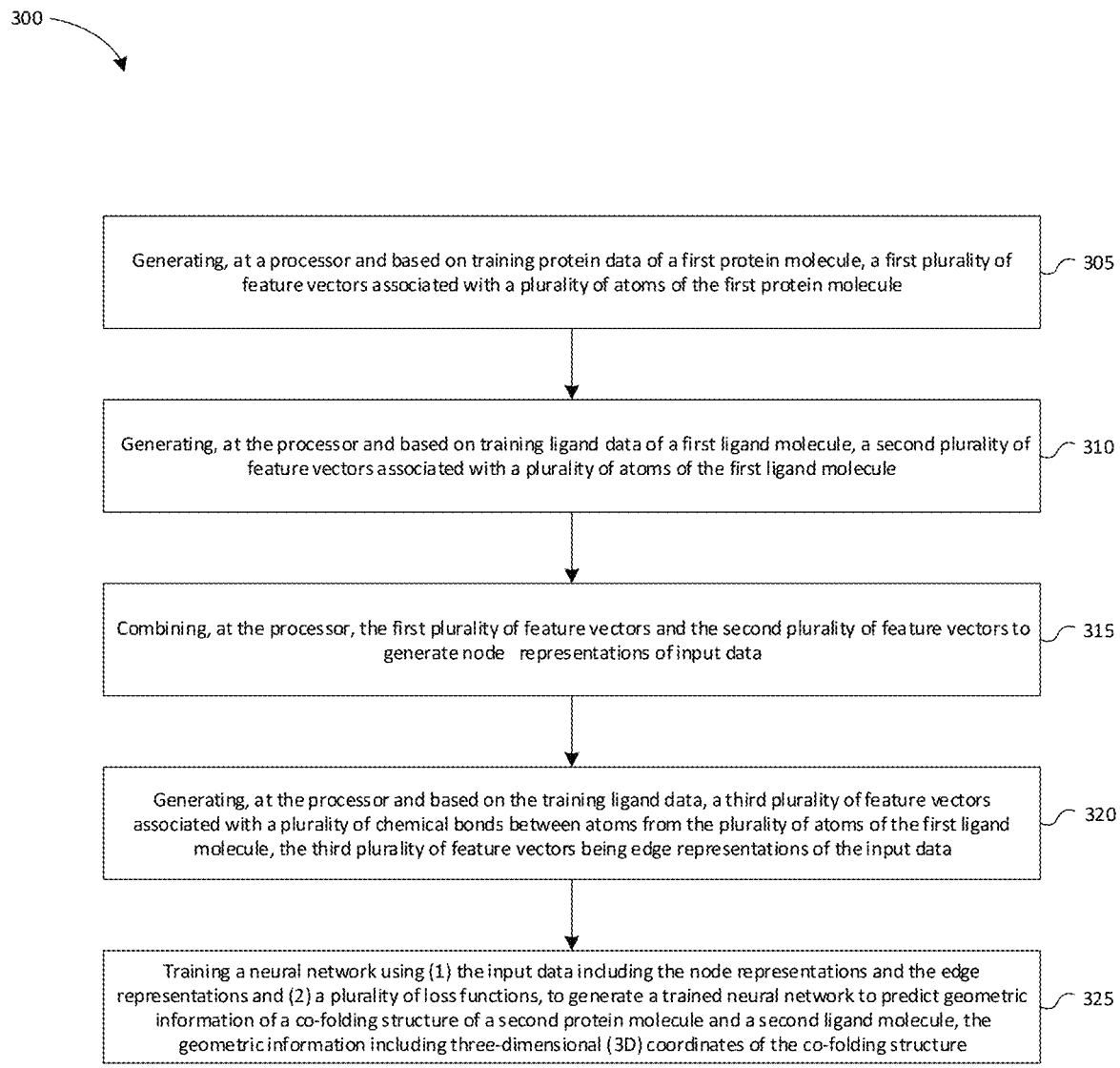
FIG. 3 is a flowchart of a method for protein-ligand structure generation using deep learning, according to an embodiment.

FIG. 3 is a flowchart of a method 300 for protein-ligand structure generation using deep learning, according to an embodiment. The method 300 includes, at 305, generating, at a processor and based on training protein data of a first protein molecule, a first plurality of feature vectors associated with a plurality of atoms of the first protein molecule. In some implementations, the method 300 can include generating input data via a data pipeline. For instance, the method 300 can include extracting 3D protein coordinates based on the first protein molecule. In some implementations, the method 300 can include embedding residues associated with the first protein molecule with protein. In some cases, generating the first plurality of feature vectors can include embedding residues associated with alpha-carbon atoms from the plurality of atoms of the first protein molecule.

At 310, the method 300 includes, generating, at the processor and based on training ligand data of a first ligand molecule, a second plurality of feature vectors associated with a plurality of atoms of the first ligand molecule. In some implementations, the method 300 can include extracting 3D ligand coordinates from the first ligand molecule to generate the second plurality of feature vectors. In some implementations, the method 300 can include generating a SMILES string defining the first ligand molecule, where the SMILES string is transformed into a molecular graph with nodes corresponding to atoms and edges corresponding to chemical bonds between atoms. In some implementations, generating the second plurality of feature vectors can include embedding a plurality of features of an atom from the plurality of atoms of the first ligand molecule into a feature vector from the second plurality of feature vectors, the plurality of features of the atom associated with (1) an aromaticity of the atom, (2) a molecular mass of the atom, (3) an atom type of the atom, (4) valence of the atom in the first ligand molecule, (5) an electronic charge of the atom, (6) stereo-chemistry of the atom around tetrahedral centers, (7) a number of hydrogen atoms connected to the atom, or (8) a hybridization of the atom At 315, the method 300 includes combining, at the processor, the first plurality of feature vectors and the second plurality of feature vectors to generate node representations of input data. In some implementations, 315 can include combining protein and ligand information to generate a single complex graph including the node representations.

At 320, the method 300 includes generating, at the processor and based on the training ligand data, a third plurality of feature vectors associated with a plurality of chemical bonds between atoms from the plurality of atoms of the first ligand molecule, the third plurality of feature vectors being edge representations of the input data. In some implementations, generating the third plurality of feature vectors can include embedding a plurality of features of a chemical bond from the plurality of chemical bonds into a feature vector from the third plurality of feature vectors, the plurality of features of the chemical bond associated with (1) stereo-chemistry of atoms of the chemical bond around tetrahedral centers, (2) multiplicity of the chemical bond, (3) aromaticity of the chemical bond, (4) conjugation of the chemical bond, (5) rotatability of the chemical bond, or (6) whether the chemical bond is associated with a ring.

At 325, the method 300 includes training a neural network using (1) the input data including the node representations and the edge representations and (2) a plurality of loss functions, to generate a trained neural network to predict geometric information of a co-folding structure of a second protein molecule and a second ligand molecule, the geometric information including three-dimensional (3D) coordinates of the co-folding structure. In some implementations, training the neural network further can include using coordinates of the plurality of atoms of the first protein molecule, in a form of a distogram. The method 300 can also include training protein data for the first protein molecule include an amino acid sequence and training protein data for the first protein molecule do not include a 3D structure of the first protein. In some implementations, the training ligand data for the first ligand molecule can include a two-dimensional (2D) representation of an atom structure of the first ligand molecule. In some implementations, the training ligand data for the first ligand molecule does not include a 3D representation of the atom structure of the first ligand molecule. In some implementations, the method can further include training the neural network using coordinates of the plurality of atoms of the first ligand molecule and re-calculating the coordinates of the plurality of atoms of the first ligand molecule, based on a loss function from the plurality of loss functions, to consider automorphism of a set of atoms from the plurality of atoms of the first ligand molecule. In some implementations, the plurality of loss functions can include at least one of (1) a Frame-Aligned Point Error function applied to the training of the neural network associated with the first protein molecule, (2) a torsion loss function applied to the training of the neural network associated with the first protein molecule, (3) a Frame Aligned Point Error function applied to the training of the neural network associated with the first ligand molecule, (4) a dihedral and angle loss function applied to the training of the neural network associated with the first ligand molecule, and/or (5) a loss function based on a N-hop distance associated with a degree of separation in a molecular graph representation of the first ligand molecule.

Figure 4:
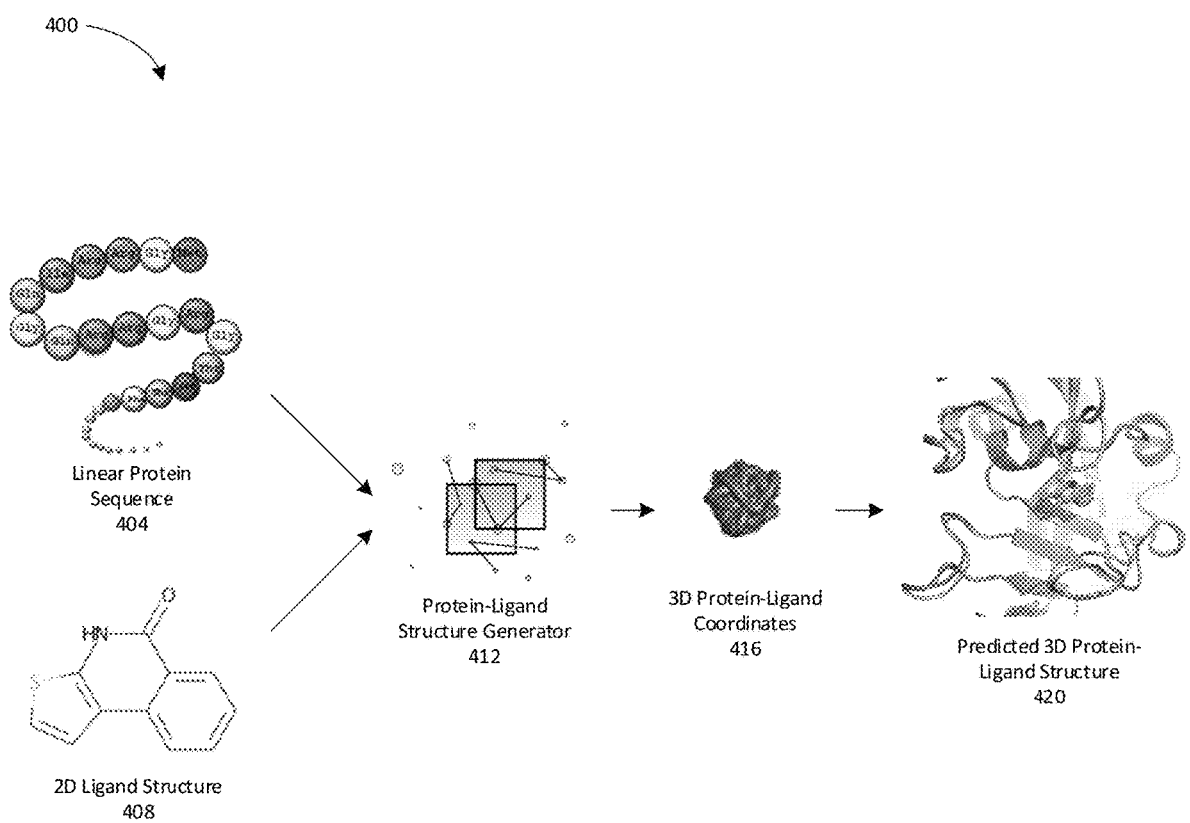
FIG. 4 is a diagrammatic flowchart of a system for the protein-ligand structure generator using deep learning, according to an embodiment.

FIG. 4 is a diagrammatic flowchart of a system 400 for the protein-ligand structure generator using deep learning, according to an embodiment. The system 400 includes a protein-ligand structure generator 412 that can receive a representation of a linear protein sequence 404 and a representation of a 2D ligand structure 408 as inputs. The protein-ligand structure generator 412 can be similar to and/or consistent with the protein-ligand structure generator 100 of FIG. 1. As shown in FIG. 4, system 400 includes illustrative representations of a protein molecule and a ligand molecule used to generate a predicted 3D protein-ligand structure 420. The representation of the linear protein sequence 404 can be similar to and/or consistent with the first protein molecule as described in FIG. 1. The representation of the linear protein sequence 404 can include, for example, a protein primary structure including a linear sequence of amino acids. Protein primary structures can be directly sequenced, or translated from DNA sequences. The 2D ligand structure 408 can include any substance that binds specifically and reversibly to a biomacromolecule to form a larger complex and alters its activity or function. In some implementations, the protein-ligand structure generator 412 can receive a linearly embedded and/or dimensionally reduced representation of the representation of the linear protein sequence 404 (e.g. the first plurality of feature vectors) and the representation of the 2D ligand structure 408 (e.g. the second plurality of feature vectors) to generate 3D protein-ligand coordinates 416. In some instances, the protein-ligand structure generator 412 can update the coordinates of the 3D protein-ligand coordinates 416 and generate a predicted 3D protein-ligand structure 420.

Figure 5:
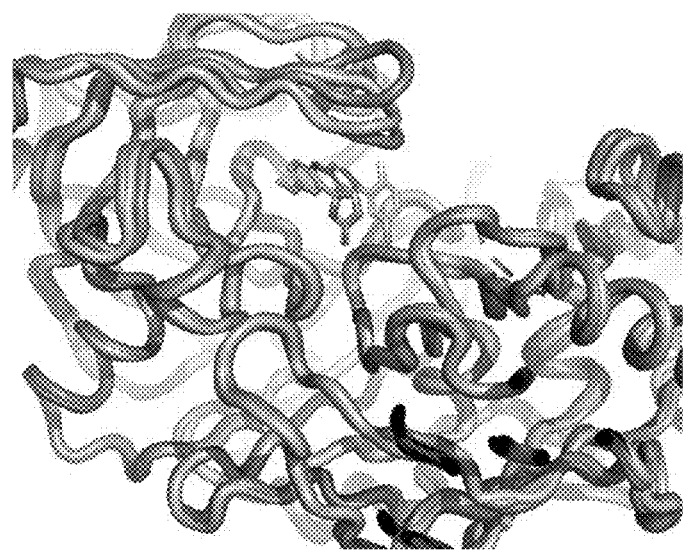
FIG. 5 is an example illustration of a 3D protein-ligand structure.

FIG. 5 is an example illustration of a 3D protein-ligand structure 500. The 3D protein-ligand structure 500 is similar to and/or consistent with any 3D protein-ligand structure generated by the 3D-invariant bond-aware edge transformer as described above. In some implementations, the 3D protein-ligand structure 500 includes an induced fit model of the 3D protein-ligand structure. The induced fit model can include, for example, a model for proper alignment for enzyme-substrate interactions. In some cases, the induced fit model can include induced fit predictions, binding site predictions, ligand pose predictions, confidence metric predictions, or the like. The 3D protein-ligand structure 500, for example, can include a co-folding structure prediction (e.g., geometric information of the co-folding structure of a protein molecule and a ligand molecule).

Figure 6:
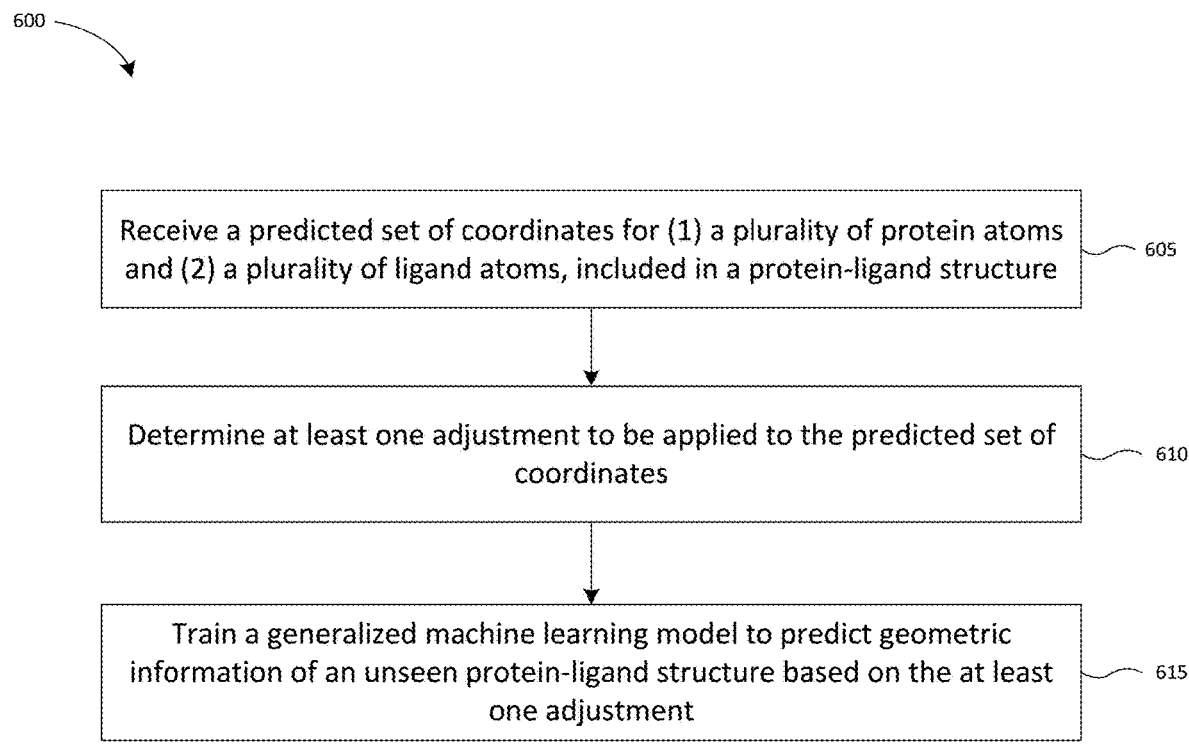
FIG. 6 is a flowchart illustrating an example method for training a machine learning model included in a protein-ligand structure generator, according to an embodiment.

FIG. 6 is a flowchart illustrating a method 600 for training a machine learning model included in a protein-ligand structure generator, according to an embodiment. At 605, the method 600 includes receiving a predicted set of coordinates for (1) a plurality of protein atoms and (2) a plurality of ligand atoms, included in a protein-ligand structure. At 610, the method 600 includes determining at least one adjustment to be applied to the predicted set of coordinates based on (a) at least one first loss function configured to determine at least one translation difference between the predicted set of coordinates and a ground-truth set of coordinates associated with the predicted set of coordinates, and (b) at least one second loss function configured to determine at least one rotational difference between the predicted set of coordinates and the ground-truth set of coordinates. At 615, the method 600 includes training a generalized machine learning model to predict geometric information of an unseen protein-ligand structure based on the at least one adjustment.

Figure 7:
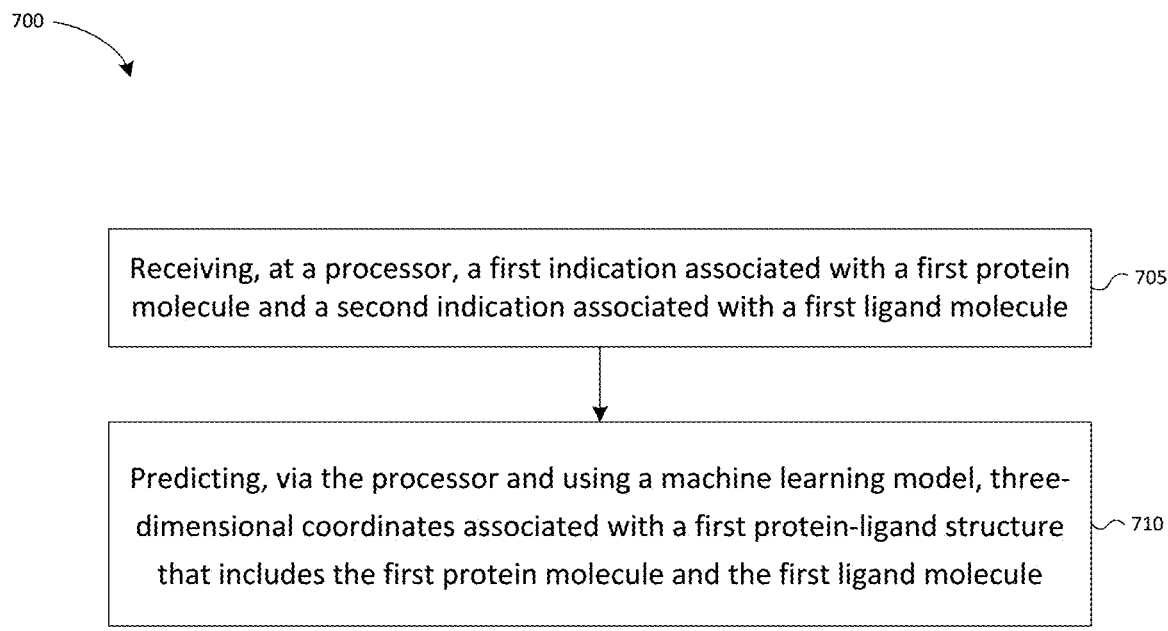
FIG. 7 is a flowchart illustrating an example method for using a machine learning model to predict three-dimensional coordinates associated with a protein-ligand structure, according to an embodiment.

FIG. 7 is a flowchart illustrating a method 700 for using a trained machine learning model to predict three-dimensional coordinates associated with a protein-ligand structure, according to an embodiment. The trained machine learning model can be trained, for example, using a method(s) discussed with respect to FIG. 6 and/or FIG. 8. At 705, the method 700 includes receiving, at a processor, a first indication associated with a first protein molecule and a second indication associated with a first ligand molecule. At 710, the method 700 includes predicting, via the first processor and using a machine learning model, three-dimensional coordinates associated with a first protein-ligand structure that includes the first protein molecule and the first ligand molecule, the machine learning model including a plurality of weights that are based on (1) a first error associated with a predicted position of a ligand atom included in a second ligand molecule from a second protein-ligand structure, the predicted position of the ligand atom being relative to a predicted position of an alpha-carbon protein atom included in a second protein molecule from the second protein-ligand structure, and (2) a second error associated with a predicted position of the alpha-carbon protein atom relative to a predicted position of a ligand atom included in the second ligand molecule.

Figure 8:
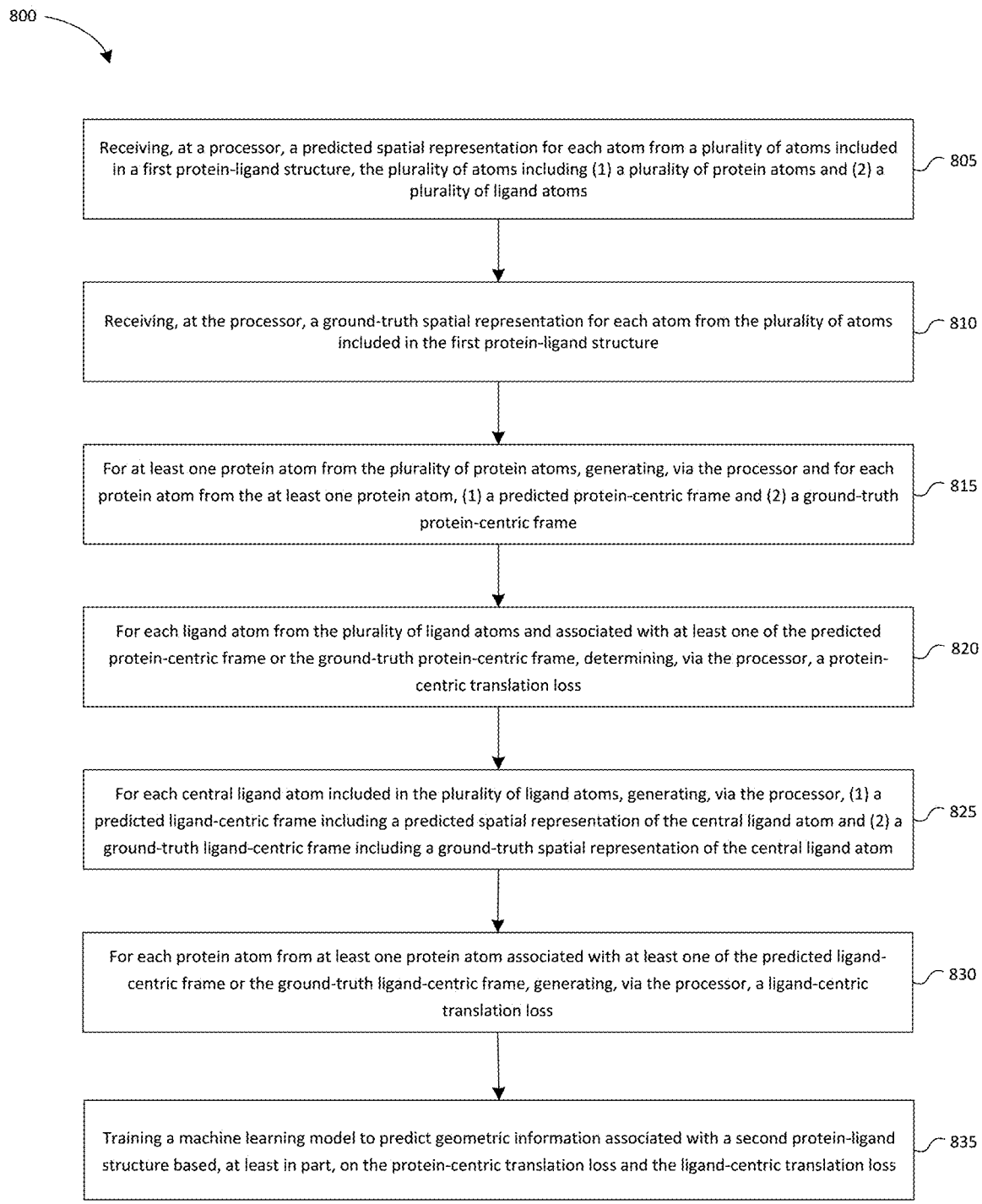
FIG. 8 is a flowchart illustrating an example method for training, based on a plurality of losses, a machine learning model included in a protein-ligand structure generator, according to an embodiment.

FIG. 8 is a flowchart illustrating a method 800 for training, based on a plurality of losses, a machine learning model included in a protein-ligand structure generator, according to an embodiment. At 805, the method 800 includes receiving, at a processor, a predicted spatial representation for each atom from a plurality of atoms included in a first protein-ligand structure, the plurality of atoms including (1) a plurality of protein atoms and (2) a plurality of ligand atoms. At 810, the method 800 includes receiving, at the processor, a ground-truth spatial representation for each atom from the plurality of atoms included in the first protein-ligand structure. For at least one protein atom from the plurality of protein atoms, at 815, the method 800 includes generating, via the processor and for each protein atom from the at least one protein atom, (1) a predicted protein-centric frame including a predicted spatial representation of the protein atom based on the predicted spatial representation of the protein atom and (2) a ground-truth protein-centric frame including a ground-truth spatial representation of the protein atom based on the ground-truth spatial representation of the protein atom. At 820, for each ligand atom from the plurality of ligand atoms and associated with at least one of the predicted protein-centric frame or the ground-truth protein-centric frame, the method 800 includes determining, via the processor, a protein-centric translation loss based on (1) the predicted spatial representation for the ligand atom relative to the predicted protein-centric frame and (2) the ground-truth spatial representation for the ligand atom relative to the ground-truth protein-centric frame. At 825, for each central ligand atom included in the plurality of ligand atoms, the method 800 includes generating, via the processor, (1) a predicted ligand-centric frame including a predicted spatial representation of the central ligand atom and based on the predicted spatial representation of the central ligand atom and (2) a ground-truth ligand-centric frame including a ground-truth spatial representation of the central ligand atom based on the ground-truth spatial representation of the central ligand atom. At 830, for each protein atom from at least one protein atom associated with at least one of the predicted ligand-centric frame or the ground-truth ligand-centric frame, the method 800 includes generating, via the processor, a ligand-centric translation loss based on (1) the predicted spatial representation for the protein atom relative to the predicted ligand-centric frame and (2) the ground-truth spatial representation for the ligand atom relative to the ground-truth ligand-centric frame. At 835, the method includes training a machine learning model to predict geometric information associated with a second protein-ligand structure based, at least in part, on the protein-centric translation loss and the ligand-centric translation loss.

In an embodiment, a non-transitory processor-readable medium stores code representing instructions to be executed by one or more processors, the instructions including code to cause the one or more processors to receive a predicted set of coordinates for (1) a plurality of protein atoms and (2) a plurality of ligand atoms, included in a protein-ligand structure. The code also causes the one or more processors to determine at least one adjustment to be applied to the predicted set of coordinates based on (a) at least one first loss function configured to determine at least one translation difference between the predicted set of coordinates and a ground-truth set of coordinates associated with the predicted set of coordinates, and (b) at least one second loss function configured to determine at least one rotational difference between the predicted set of coordinates and the ground-truth set of coordinates. The code also causes the one or more processors to train a generalized machine learning model to predict geometric information of an unseen protein-ligand structure based on the at least one adjustment.

In some implementations, the at least one second loss function can include at least one of (1) a third loss function configured to determine at least one torsion angle difference between the predicted set of coordinates and the ground-truth set of coordinates, each torsion angle difference from the at least one torsion angle difference being associated with a bond torsion angle between at least two protein atoms from the plurality of protein atoms; (2) a fourth loss function configured to determine at least one dihedral difference between the predicted set of coordinates and the ground-truth set of coordinates, each dihedral difference from the at least one dihedral difference being associated with a bond torsion between at least two ligand atoms from the plurality of protein atoms; or (3) a fifth loss function configured to determine at least one bond angle difference between the predicted set of coordinates and the ground-truth set of coordinates, each bond angle difference from the at least one bond angle difference being associated with a bond angle between at least two ligand atoms from the plurality of protein atoms.

In some implementations, at least one of the fourth loss function or the fifth loss function can include a von Mises dihedral angle log-likelihood function. In some implementations, the at least one adjustment can be determined based further on a third loss function configured to determine a plausibility of at least one path based on a path distance difference between the predicted set of coordinates and the ground-truth set of coordinates. In some implementations, the at least one first loss function can include (1) a first comparison, between the predicted set of coordinates and the ground-truth set of coordinates, of a first position of a first ligand atom from the plurality of ligand atoms relative to a first protein atom from the plurality of protein atoms and (2) a second comparison, between the predicted set of coordinates and the ground-truth set of coordinates, of a second position of a second protein atom from the plurality of protein atoms relative to a second ligand atom from the plurality of ligand atoms.

In some implementations, the first protein atom can be a first protein alpha-carbon atom, the second protein atom can be a second protein alpha-carbon atom, the second ligand atom can be a first central ligand atom, and the at least one first loss function can further include (1) a third comparison, between the predicted set of coordinates and the ground-truth set of coordinates, of a third position of a third ligand atom from the plurality of ligand atoms relative to a first sidechain protein atom from the plurality of protein atoms and (2) a fourth comparison, between the predicted set of coordinates and the ground-truth set of coordinates, of a fourth position of a second sidechain protein atom from the plurality of protein atoms relative to a second central ligand atom from the plurality of ligand atoms.

In an embodiment, a method includes receiving, at a processor, a first indication associated with a first protein molecule and a second indication associated with a first ligand molecule. The method also includes predicting, via the first processor and using a machine learning model, three-dimensional coordinates associated with a first protein-ligand structure that includes the first protein molecule and the first ligand molecule, the machine learning model including a plurality of weights that are based on (1) a first error associated with a predicted position of a ligand atom included in a second ligand molecule from a second protein-ligand structure, the predicted position of the ligand atom being relative to a predicted position of an alpha-carbon protein atom included in a second protein molecule from the second protein-ligand structure, and (2) a second error associated with a predicted position of the alpha-carbon protein atom relative to a predicted position of a ligand atom included in the second ligand molecule.

In some implementations, the plurality of weights can be based further on a third error associated with a predicted position of a sidechain protein atom included in the second protein molecule, the predicted position of the sidechain protein atom being relative to the predicted position of the ligand atom. In some implementations the predicted position of the ligand atom can be a first predicted position, and the plurality of weights can be based further on a third error associated with a second predicted position of the ligand atom relative to a predicted position of a sidechain protein atom included in the second protein molecule. In some implementations, the ligand atom can be bonded to two additional ligand atoms and is a central ligand atom. In some implementations, the first error can be iteratively determined based on each alpha-carbon protein atom from a plurality of alpha-carbon protein atoms included in the second protein molecule. Additionally, the second error can be iteratively determined based on each central ligand atom from a plurality of central ligand atoms included in the second ligand molecule.

In some implementations, the plurality of weights can be based further on at least one third error that is associated with at least one ligand atom included in the second ligand molecule and that is not associated with a protein atom included in the second protein molecule. In some implementations, the at least one third error can be determined based on at least one of an N-hop distance loss, a bond angle loss, or a dihedral loss.

In an embodiment, a method includes receiving, at a processor, a predicted spatial representation for each atom from a plurality of atoms included in a first protein-ligand structure, the plurality of atoms including (1) a plurality of protein atoms and (2) a plurality of ligand atoms. The method also includes receiving, at the processor, a ground-truth spatial representation for each atom from the plurality of atoms included in the first protein-ligand structure. For at least one protein atom from the plurality of protein atoms, the method also includes generating, via the processor and for each protein atom from the at least one protein atom, (1) a predicted protein-centric frame including a predicted spatial representation of the protein atom based on the predicted spatial representation of the protein atom and (2) a ground-truth protein-centric frame including a ground-truth spatial representation of the protein atom based on the ground-truth spatial representation of the protein atom. For each ligand atom from the plurality of ligand atoms and associated with at least one of the predicted protein-centric frame or the ground-truth protein-centric frame, the method also includes determining, via the processor, a protein-centric translation loss based on (1) the predicted spatial representation for the ligand atom relative to the predicted protein-centric frame and (2) the ground-truth spatial representation for the ligand atom relative to the ground-truth protein-centric frame. For each central ligand atom included in the plurality of ligand atoms, the method includes generating, via the processor, (1) a predicted ligand-centric frame including a predicted spatial representation of the central ligand atom and based on the predicted spatial representation of the central ligand atom and (2) a ground-truth ligand-centric frame including a ground-truth spatial representation of the central ligand atom based on the ground-truth spatial representation of the central ligand atom. For each protein atom from at least one protein atom associated with at least one of the predicted ligand-centric frame or the ground-truth ligand-centric frame, the method includes generating, via the processor, a ligand-centric translation loss based on (1) the predicted spatial representation for the protein atom relative to the predicted ligand-centric frame and (2) the ground-truth spatial representation for the ligand atom relative to the ground-truth ligand-centric frame. The method also includes training a machine learning model to predict geometric information associated with a second protein-ligand structure based, at least in part, on the protein-centric translation loss and the ligand-centric translation loss.

In some implementations, the at least one protein atom can include at least one alpha-carbon protein atom and excludes any sidechain protein atoms. In some implementations, the at least one protein atom can include at least one sidechain protein atom. In some implementations, the method can further include generating a ligand-only loss based on the predicted spatial representation for each ligand atom and the ground-truth spatial representation for each ligand atom, the training the machine learning model being further based, at least in part, on the ligand-only loss. In some implementations, the ligand-only loss can include a N-hop distance loss configured to determine a plausibility of a bond between at least two ligand atoms from the plurality of ligand atoms. In some implementations, the ligand-only loss can include a bond angle loss that is determined for at least one bond between at least two ligand atoms from the plurality of ligand atoms. In some implementations, the ligand-only loss can include a dihedral loss that is associated with at least one bond torsion for at least one bond between at least two ligand atoms from the plurality of ligand atoms.

It is to be noted that any one or more of the aspects and embodiments described herein can be conveniently implemented using one or more machines (e.g., one or more compute devices that are utilized as a user compute device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules can also include appropriate hardware for assisting in the implementation of the machine executable instructions of the software and/or software module.

Such software can be a computer program product that employs a machine-readable storage medium. A machine-readable storage medium can be any medium that is capable of storing and/or encoding a sequence of instructions for execution by a machine (e.g., a compute device 104) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software can also include information (e.g., data) carried as a data signal on a data carrier, such as a carrier wave. For example, machine-executable information can be included as a data-carrying signal embodied in a data carrier in which the signal encodes a sequence of instruction, or portion thereof, for execution by a machine (e.g., a compute device) and any related information (e.g., data structures and data) that causes the machine to perform any one of the methodologies and/or embodiments described herein.

Examples of a compute device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a compute device can include and/or be included in a kiosk.

All combinations of the foregoing concepts and additional concepts discussed herewithin (provided such concepts are not mutually inconsistent) are contemplated as being part of the subject matter disclosed herein. The terminology explicitly employed herein that also can appear in any disclosure incorporated by reference should be accorded a meaning most consistent with the particular concepts disclosed herein.

The drawings are primarily for illustrative purposes, and are not intended to limit the scope of the subject matter described herein. The drawings are not necessarily to scale; in some instances, various aspects of the subject matter disclosed herein can be shown exaggerated or enlarged in the drawings to facilitate an understanding of different features. In the drawings, like reference characters generally refer to like features (e.g., functionally similar and/or structurally similar elements).

The entirety of this application (including the Cover Page, Title, Headings, Background, Summary, Brief Description of the Drawings, Detailed Description, Embodiments, Abstract, Figures, Appendices, and otherwise) shows, by way of illustration, various embodiments in which the embodiments can be practiced. The advantages and features of the application are of a representative sample of embodiments only, and are not exhaustive and/or exclusive. Rather, they are presented to assist in understanding and teach the embodiments, and are not representative of all embodiments. As such, certain aspects of the disclosure have not been discussed herein. That alternate embodiments cannot have been presented for a specific portion of the innovations or that further undescribed alternate embodiments can be available for a portion is not to be considered to exclude such alternate embodiments from the scope of the disclosure. It will be appreciated that many of those undescribed embodiments incorporate the same principles of the innovations and others are equivalent. Thus, it is to be understood that other embodiments can be utilized and functional, logical, operational, organizational, structural and/or topological modifications can be made without departing from the scope and/or spirit of the disclosure. As such, all examples and/or embodiments are deemed to be non-limiting throughout this disclosure.

Also, no inference should be drawn regarding those embodiments discussed herein relative to those not discussed herein other than it is as such for purposes of reducing space and repetition. For example, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure.

The phrase "based on" does not mean "based only on," unless expressly specified otherwise. In other words, the phrase "based on" describes both "based only on" and "based at least on."

The term "processor" should be interpreted broadly to encompass a general-purpose processor, a central processing unit (CPU), a microprocessor, a digital signal processor (DSP), a controller, a microcontroller, a state machine and so forth. Under some circumstances, a "processor" can refer to an application specific integrated circuit (ASIC), a programmable logic device (PLD), a field programmable gate array (FPGA), etc. The term "processor" can refer to a combination of processing devices, e.g., a combination of a DSP and a microprocessor, multiple microprocessors, one or more microprocessors in conjunction with a DSP core or any other such configuration.

The term "memory" should be interpreted broadly to encompass any electronic component capable of storing electronic information. The term memory can refer to various types of processor-readable media such as random-access memory (RAM), read-only memory (ROM), non-volatile random-access memory (NVRAM), programmable read-only memory (PROM), erasable programmable read only memory (EPROM), electrically erasable PROM (EEPROM), flash memory, magnetic or optical data storage, registers, etc. Memory is said to be in electronic communication with a processor if the processor can read information from and/or write information to the memory. Memory that is integral to a processor is in electronic communication with the processor.

The terms "instructions" and "code" should be interpreted broadly to include any type of computer-readable statement(s). For example, the terms "instructions" and "code" can refer to one or more programs, routines, subroutines, functions, procedures, etc. "Instructions" and "code" can comprise a single computer-readable statement or many computer-readable statements.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) can be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules can include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Various concepts can be embodied as one or more methods, of which at least one example has been provided. The acts performed as part of the method can be ordered in any suitable way. Accordingly, embodiments can be constructed in which acts are performed in an order different than illustrated, which can include performing some acts simultaneously, even though shown as sequential acts in illustrative embodiments. Put differently, it is to be understood that such features can not necessarily be limited to a particular order of execution, but rather, any number of threads, processes, services, servers, and/or the like that can execute serially, asynchronously, concurrently, in parallel, simultaneously, synchronously, and/or the like in a manner consistent with the disclosure. As such, some of these features can be mutually contradictory, in that they cannot be simultaneously present in a single embodiment. Similarly, some features are applicable to one aspect of the innovations, and inapplicable to others.

In addition, the disclosure can include other innovations not presently described. Applicant reserves all rights in such innovations, including the right to embodiment such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein can be implemented in a manner that enables a great deal of flexibility and customization as described herein.

All definitions, as defined and used herein, should be understood to control over dictionary definitions, definitions in documents incorporated by reference, and/or ordinary meanings of the defined terms.

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method, comprising:
receiving, at a processor, a predicted spatial representation for each atom from a plurality of atoms included in a first protein-ligand structure, the plurality of atoms including (1) a plurality of protein atoms and (2) a plurality of ligand atoms;
receiving, at the processor, a ground-truth spatial representation for each atom from the plurality of atoms included in the first protein-ligand structure;
for at least one protein atom from the plurality of protein atoms:
generating, via the processor and for each protein atom from the at least one protein atom, (1) a predicted protein-centric frame based on the predicted spatial representation of the protein atom and (2) a ground-truth protein-centric frame based on the ground-truth spatial representation of the protein atom, and
for each ligand atom that is from the plurality of ligand atoms and that is associated with at least one of the predicted protein-centric frame or the ground-truth protein-centric frame:
generating, via the processor, a protein-centric translation loss based on (1) the predicted spatial representation for the ligand atom relative to the predicted protein-centric frame and (2) the ground-truth spatial representation for the ligand atom relative to the ground-truth protein-centric frame, to produce a set of protein-centric translation losses;
for each central ligand atom included in the plurality of ligand atoms:
generating, via the processor, (1) a predicted ligand-centric frame based on the predicted spatial representation of the central ligand atom and (2) a ground-truth ligand-centric frame based on the ground-truth spatial representation of the central ligand atom, and
for each protein atom from at least one protein atom associated with at least one of the predicted ligand-centric frame or the ground-truth ligand-centric frame:
generating, via the processor, a ligand-centric translation loss based on (1) the predicted spatial representation for the protein atom relative to the predicted ligand-centric frame and (2) the ground-truth spatial representation for the ligand atom relative to the ground-truth ligand-centric frame, to produce a set of ligand-centric translation losses; and
training a machine learning model to produce a trained machine learning model that is configured to predict a plurality of coordinates associated with a second protein-ligand structure based on the set of protein-centric translation losses and the set of ligand-centric translation losses.

2. The method of claim 1, wherein the at least one protein atom includes at least one alpha-carbon protein atom and excludes any sidechain protein atoms.

3. The method of claim 1, wherein the at least one protein atom includes at least one sidechain protein atom.

4. The method of claim 1, further comprising:
generating a ligand-only loss based on the predicted spatial representation for each ligand atom and the ground-truth spatial representation for each ligand atom, the training the machine learning model being further based, at least in part, on the ligand-only loss.

5. The method of claim 4, wherein the ligand-only loss includes a N-hop distance loss configured to determine a plausibility of a bond between at least two ligand atoms from the plurality of ligand atoms.

6. The method of claim 4, wherein the ligand-only loss includes a bond angle loss that is determined for at least one bond between at least two ligand atoms from the plurality of ligand atoms.

7. The method of claim 4, wherein the ligand-only loss includes a dihedral loss that is associated with at least one bond torsion for at least one bond between at least two ligand atoms from the plurality of ligand atoms.

8. A non-transitory processor-readable medium storing code representing instructions to be executed by one or more processors, the instructions comprising code to cause the one or more processors to:
receive a predicted spatial representation for each atom from a plurality of atoms included in a first protein-ligand structure, the plurality of atoms including (1) a plurality of protein atoms and (2) a plurality of ligand atoms;
receive a ground-truth spatial representation for each atom from the plurality of atoms included in the protein-ligand structure;
for at least one protein atom from the plurality of protein atoms:
generate, for each protein atom from the at least one protein atom, (1) a predicted protein-centric frame including a predicted spatial representation of the protein atom based on the predicted spatial representation of the protein atom and (2) a ground-truth protein-centric frame including a ground truth spatial representation of the protein atom based on the ground-truth spatial representation of the protein atom, and for each ligand atom from the plurality of ligand atoms and associated with at least one of the predicted protein-centric frame or the ground-truth protein-centric frame:

generate a protein-centric translation loss based on (1) the predicted spatial representation for the ligand atom relative to the predicted protein-centric frame and (2) the ground-truth spatial representation for the ligand atom relative to the ground-truth protein-centric frame, to produce a set of protein-centric translation losses;

for each central ligand atom included in the plurality of ligand atoms:

generate (1) a predicted ligand-centric frame based on the predicted spatial representation of the central ligand atom and (2) a ground-truth ligand-centric frame based on the ground-truth spatial representation of the central ligand atom, and for each protein atom from at least one protein atom associated with at least one of the predicted ligand-centric frame or the ground-truth ligand-centric frame:

generate a ligand-centric translation loss based on (1) the predicted spatial representation for the protein atom relative to the predicted ligand-centric frame and (2) the ground-truth spatial representation for the ligand atom relative to the ground-truth ligand-centric frame, to produce a set of ligand-centric translation losses; and train a machine learning model to produce a trained machine learning model that is configured to predict a plurality of coordinates associated with a second protein-ligand structure based on the set of protein-centric translation losses and the set of ligand-centric translation losses.

9. The non-transitory processor-readable medium of claim 8, wherein the at least one protein atom includes at least one alpha-carbon protein atom and excludes any sidechain protein atoms.

10. The non-transitory processor-readable medium of claim 8, wherein the at least one protein atom includes at least one sidechain protein atom.

11. The non-transitory processor-readable medium of claim 8, wherein the instructions further comprise code to cause the one or more processors to:

generate a ligand-only loss based on the predicted spatial representation for each ligand atom and the ground-truth spatial representation for each ligand atom, the training the machine learning model being further based, at least in part, on the ligand-only loss.

12. The non-transitory processor-readable medium of claim 11, wherein the ligand-only loss includes a N-hop distance loss configured to determine a plausibility of a bond between at least two ligand atoms from the plurality of ligand atoms.

13. The non-transitory processor-readable medium of claim 11, wherein the ligand-only loss includes a bond angle loss that is determined for at least one bond between at least two ligand atoms from the plurality of ligand atoms.

14. The non-transitory processor-readable medium of claim 11, wherein the ligand-only loss includes a dihedral loss that is associated with at least one bond torsion for at least one bond between at least two ligand atoms from the plurality of ligand atoms.

15. An apparatus, comprising:
a processor; and
a memory coupled to the processor, the memory storing instructions that, when executed by the processor, cause the processor to:

receive a predicted spatial representation for each atom from a plurality of atoms included in a first protein-ligand structure, the plurality of atoms including (1) a plurality of protein atoms and (2) a plurality of ligand atoms;

receive a ground-truth spatial representation for each atom from the plurality of atoms included in the protein-ligand structure;

for at least one protein atom from the plurality of protein atoms:

generate, for each protein atom from the at least one protein atom, (1) a predicted protein-centric frame based on the predicted spatial representation of the protein atom and (2) a ground-truth protein-centric frame based on the ground-truth spatial representation of the protein atom, and for each ligand atom that is from the plurality of ligand atoms and that is associated with at least one of the predicted protein-centric frame or the ground-truth protein-centric frame:

generate a protein-centric translation loss based on (1) the predicted spatial representation for the ligand atom relative to the predicted protein-centric frame and (2) the ground-truth spatial representation for the ligand atom relative to the ground-truth protein-centric frame, to produce a set of protein-centric translation losses;

for each central ligand atom included in the plurality of ligand atoms:

generate (1) a predicted ligand-centric frame including a predicted spatial representation of the central ligand atom and based on the predicted spatial representation of the central ligand atom and (2) a ground-truth ligand-centric frame including a ground truth spatial representation of the central ligand atom based on the ground-truth spatial representation of the central ligand atom, and for each protein atom from at least one protein atom associated with at least one of the predicted ligand-centric frame or the ground-truth ligand-centric frame:

generate a ligand-centric translation loss based on (1) the predicted spatial representation for the protein atom relative to the predicted ligand-centric frame and (2) the ground-truth spatial representation for the ligand atom relative to the ground-truth ligand-centric frame, to produce a set of ligand-centric translation losses; and train a machine learning model to predict a plurality of coordinates associated with a second protein-ligand structure based on the set of protein-centric translation losses and the set of ligand-centric translation losses.

16. The apparatus of claim 15, wherein the at least one protein atom includes at least one alpha-carbon protein atom and excludes any sidechain protein atoms.

17. The apparatus of claim 15, wherein the at least one protein atom includes at least one sidechain protein atom.

18. The apparatus of claim 15, wherein the memory storing further instructions that, when executed by the processor, cause the processor to:
generate a ligand-only loss based on the predicted spatial representation for each ligand atom and the ground-truth spatial representation for each ligand atom, the training the machine learning model being further based, at least in part, on the ligand-only loss.

19. The apparatus of claim 18, wherein the ligand-only loss includes a N-hop distance loss configured to determine a plausibility of a bond between at least two ligand atoms from the plurality of ligand atoms.

20. The apparatus of claim 18, wherein the ligand-only loss includes a bond angle loss that is determined for at least one bond between at least two ligand atoms from the plurality of ligand atoms.

\* \* \* \* \*